(12) United States Patent
Shmatukha et al.

(10) Patent No.: US 9,095,273 B2
(45) Date of Patent: Aug. 4, 2015

(54) SYSTEMS AND METHODS FOR AUTOMATED DYNAMIC CONTRAST ENHANCEMENT IMAGING

(75) Inventors: Andriy Shmatukha, Toronto (CA); Eugene Crystal, Toronto (CA)

(73) Assignee: SUNNYBROOK RESEARCH INSTITUTE, Toronto, ON (CA)

( * ) Notice: Subject to any disclaimer, the term of this patent is extended or adjusted under 35 U.S.C. 154(b) by 932 days.

(21) Appl. No.: 13/245,591

(22) Filed: Sep. 26, 2011

(65) Prior Publication Data

US 2013/0079626 A1   Mar. 28, 2013

(51) Int. Cl.
*A61B 5/05*   (2006.01)
*A61B 5/055*   (2006.01)
*A61B 6/03*   (2006.01)
(Continued)

(52) U.S. Cl.
CPC . *A61B 5/055* (2013.01); *A61B 6/03* (2013.01); *A61B 6/481* (2013.01); *A61B 6/5205* (2013.01); *A61B 8/481* (2013.01); *A61B 8/5207* (2013.01); *G06T 7/0016* (2013.01); *G06T 7/0081* (2013.01); *G06T 7/0097* (2013.01); *G06T 2207/10016* (2013.01); *G06T 2207/10096* (2013.01); *G06T 2207/20148* (2013.01); *G06T 2207/30048* (2013.01); *G06T 2207/30096* (2013.01)

(58) Field of Classification Search
CPC .......... A61B 5/055; A61B 6/03; A61B 6/481; A61B 6/5205; A61B 8/481; A61B 8/5207; G06T 7/0081; G06T 7/0097; G06T 7/0016; G06T 2207/30096; G06T 2207/10016; G06T 2207/10096; G06T 2207/20148; G06T 2207/30048

USPC ......................................................... 600/420
See application file for complete search history.

(56) References Cited

U.S. PATENT DOCUMENTS 5,373,844 A * 12/1994 Smith et al. .................. 600/427
5,459,769 A * 10/1995 Brown ............................. 378/4
(Continued)

OTHER PUBLICATIONS

Jayaweera et al., Quantification of images obtained during myocardial contrast echocardiography, Echocardiography. Jul. 1994;11(4):385-96.*
(Continued)

*Primary Examiner* — Bo J Peng
(74) *Attorney, Agent, or Firm* — Lynn C. Schumacher; Stephen W. Leonard; Hill & Schumacher

(57) ABSTRACT

Embodiments disclosed herein provide systems and methods for automating the acquisition and analysis of contrast enhancement images. Model-free discrimination methods are provided in which discrimination between well-perfused pixels (e.g. normal tissue) and perfusion-deficient pixels (e.g. ablation lesions) is automated based on histogram shape. For example, in selected embodiments, discrimination is made based on pixels corresponding to abnormal perfusion (e.g. ablation lesions) and normal perfusion (e.g. normal tissue) form distinctive lobes separated by a minimum formed due to the presence of border pixels. Segmentation of cumulative dynamic contrast enhancement maps by thresholds identified on such histograms is employed to separate abnormally-perfused tissue from the normally-perfused tissue without any user interactions, freeing the user from the necessity to analyze and interpret original dynamic contrast enhancement images or maps derived from them. The histogram properties can also be used for automatic termination of the image acquisition and analysis processes.

37 Claims, 25 Drawing Sheets

(51) Int. Cl.
*A61B 6/00* (2006.01)
*A61B 8/08* (2006.01)
*G06T 7/00* (2006.01)

(56) References Cited

U.S. PATENT DOCUMENTS

| | | | | |
|---|---|---|---|---|
| 2002/0072667 | A1* | 6/2002 | Kucharczyk et al. | 600/419 |
| 2003/0161548 | A1* | 8/2003 | Vuylsteke | 382/274 |
| 2010/0166276 | A1* | 7/2010 | Dube et al. | 382/131 |

OTHER PUBLICATIONS

Shmatukha et al. Visualization of Ablation Lesions by Dynamic Contrast Enhanced MRI. Applied Science Laboratory. GE Healthcare. Ca. Sunnybrook Health Sciences Centre. Ca, Year 2011 is shown in NPL p. 2/16.

Shmatukha et al. Visualization of Ablation Lesions by Dynamic Contrast-Enhanced (DynCE) MRI. Journal of Cardiovascular Magnetic Resonance. pp. 1-4, Year 2010 is shown in the NPL provided on p. 1.

Shmatukha et al. Visualization of Ablation Lesions by Dynamic Contrast-Enhanced (DynCE) MRI. GE Imagination at work. Sunnybrook Health Sciences Centre. 21/21. E-Poster#4151, ISMRM-2010, Sep. 12, 2011.

Shmatukha et al. Visualization of Ablation Lesions by Dynamic Contrast-Enhanced (DynCE) MRI. GE Imagination at work. Sunnybrook Health Sciences Centre. 28/16. andriy.shmatukha@ge.com. Sep. 12, 2011.

Andriy Shmatukha, Bharathi Sundaram, Xiuling Qi, Samuel Oduneye, Jeffrey Stainsby, Graham Wright, Eugene Crystal, "Visualization of Ablation Lesions by Dynamic Contrast-Enhanced (DynCE) MRI"; Proceedings of the Joint Annual Meeting ISMRM-ESMRMB 2010, May 1-7, 2010, Stockholm, Sweden.

Andriy Shmatukha, Bharathi Sundaram, Xiuling Qi, Samuel Oduneye, Jeffrey Stainsby, Graham Wright, Eugene Crystal, "Visualization of Ablation Lesions by Dynamic Contrast-Enhanced (DynCE) MRI"; Joint Annual Meeting ISMRM-ESMRMB 2010, May 1-7, 2010, Stockholm, Sweden (Poster Presentation).

Andriy Shmatukha, Xiuling Qi, Sudip Ghate, Mihaela Pop, Jennifer Barry, Samuel Oduneye, Jeffrey Stainsby, Graham Wright, Eugene Crystal, "Visualization of ablation lesions by dynamic contrast-enhanced MRI"; Proceedings of the 8th Interventional MRI Symposium, Sep. 24-25, 2010, Leipzig, Germany; V-16, pp. 60-62.

Andriy Shmatukha and Eugene Crystal, "Algorithm for automatic segmentation of ablation lesions and termination of the image acquisition/analysis process"; Society for Cardiac Magnetic Resonance; 2011 SCMR/Euro CMR Joint Scientific Sessions; Feb. 3, 2011, Nice, France (Poster presentation).

Andriy Shmatukha, Xiuling Qi, Sudip Ghate, Mihaela Pop, Jennifer Barry, Samuel Oduneye, Jeffrey Stainsby, Graham Wright, Eugene Crystal, "Visualization of ablation lesions by dynamic contrast-enhanced MRI"; 8th Interventional MRI Symposium, Sep. 24, 2010, Leipzig, Germany (Oral Presentation).

Andriy Shmatukha, Bharathi Sundaram, Xiuling Qi, Samuel Oduneye, Jeffrey Stainsby, Graham Wright, Eugene Crystal, "Visualization of Ablation Lesions by Dynamic Contrast-Enhanced (DynCE) MRI"; Proceedings of the Society for Cardiac Magnetic Resonance; 13th Annual SCMR Scientific Sessions, Phoenix, AZ, USA. Jan. 21-24, 2010; Journal of Cardiovascular Magnetic Resonance 2010, 12 (Suppl. 1): O25.

Andriy Shmatukha, Bharathi Sundaram, Xiuling Qi, Samuel Oduneye, Jeffrey Stainsby, Graham Wright, Eugene Crystal, "Visualization of Ablation Lesions by Dynamic Contrast-Enhanced (DynCE) MRI"; Society for Cardiac Magnetic Resonance; 13th Annual SCMR Scientific Sessions, Phoenix, AZ, USA. Jan. 22, 2010 (Poster Presentation).

Andriy Shmatukha and Eugene Crystal, "Algorithm for automatic segmentation of ablation lesions and termination of the image acquisition/analysis process"; Proceedings the Society for Cardiac Magnetic Resonance; 2011 SCMR/Euro CMR Joint Scientific Sessions; Feb. 3-6, 2011, Nice, France. Journal of Cardiovascular Magnetic Resonance 2011; 13 (Suppl. 1): P245.

* cited by examiner

SYSTEMS AND METHODS FOR AUTOMATED DYNAMIC CONTRAST ENHANCEMENT IMAGING

BACKGROUND

The present disclosure is related to contrast enhanced medical imaging. In cardiac electrophysiology (EP), transcatheter radiofrequency (RF) thermal ablations aim for the elimination and/or electrical isolation of the arrhythmia substrate by creating closed loops of thermally ablated tissue. Ablation lesion contiguity and inclusiveness define the procedural long-term success.

Currently, EP procedures are performed under x-ray, electro-anatomical voltage mapping (EAVM) and intra-cardiac echo (ICE) guidance. All these modalities do not provide adequate soft tissue visualization to the electrophysiologist. Hence, there is a substantial and constantly growing interest among the electrophysiologists in using MRI for ablation outcome verification both intra- and post-operatively.

Previously reported studies investigated EP lesion appearance on T1w, T2w (1), delayed enhancement (DE, 2-5) MR imaging, and their combination (6). They proved the feasibility of using MRI techniques for the visualization of fresh and aged ablation lesions. However, these T1w/T2w-based imaging methods provide low contrast between the ablation lesion and surrounding normal tissue. Also, they required rather long imaging times, which handicaps its potential intra-operative applicability. In addition, the current T1w/T2w-based imaging does not have a plausible biological explanation for changes in the MRI appearance of ablation lesions during repetitive imaging post-procedurally (7).

In contrary, contrast agent enhanced (CE) MR imaging has proven to be an accurate and reliable indicator of tissue destruction during thermal ablations (8), corresponding well not only to the histopathological analysis (9), but also to the delivered thermal dose (10, 11). However, delayed contrast enhancement (DE) MR imaging of ablation lesions also requires long waiting (after contrast agent injection) as well as long scanning times, which complicates its intraoperative applications. In addition, ablation lesions' appearance on DE MRI is highly influenced by the time elapsed after contrast agent injection (3) and imaging resolution (7), and thus is difficult to interpret. These drawbacks of the traditional MRI ablation lesion visualization methods are especially pronounced when the goal of the visualization process is not simply to confirm the fact of the existence of ablation lesions per se, but rather to delineate the lesions' borders in order to identify the gaps between them. Indeed, accurate delineation of the outer borders of ablation lesions is the main motivation for intra- and post-operative MR imaging during cardiac ablative procedures.

Dynamic contrast enhancement MRI is an improved method involving the sampling of the process of contrast agent arrival and passage through the tissue per se, and thus does not require long waiting times after contrast agent injection. It has been successfully applied for ablation lesion visualization and characterization (12, 13) as well as for tumor perfusion (14, 15) and viability (16, 17) assessment. Dynamic contrast enhancement MRI is based on the differences in perfusion properties between different tissues or areas of the same tissue—e.g., the lack of perfusion in the tissue areas affected by ablation (due to the occlusion and/or disruption of its vascular structures), which can potentially lead to apoptosis, especially in the myocardium. However, the existing methods of dynamic contrast enhancement image analysis are not suitable for intra- and post-operative imaging during cardiac EP procedures. They rely upon model-based fitting of pixel enhancement curves with certain properties and thus require the whole contrast agent wash-in and wash-out processes to be sampled with high signal-to-noise ratio (SNR). Such requirements not only result in longer MRI scan times, but are also very difficult to satisfy in cardiac MRI restricted by the respiratory and cardiac motion patterns of the imaged anatomy.

Preliminary investigations have indicated (18) that these limitations can be overcome by combining various instantaneous pixel intensity evolution characteristics at each dynamic contrast enhancement sampling instant into cumulative maps, which reflect not only the current signal evolution state of each represented pixel, but also the whole "pre-history" of the pixel, and hence reflect the dynamic contrast enhancement process in general rather its current instantaneous state only. This helps to differentiate between pixels with different contrast enhancement properties, whose differences may be hidden by the image acquisition noise. As a result, such maps are relatively immune to low SNR (which makes them suitable for fast cardiac imaging), and require imaging during only a relatively short time following contrast agent injection to delineate ablation lesion borders without any model-based fitting of curves with special properties anticipated in advance.

Unfortunately, the intra-operative interpretation of dynamic contrast enhancement images, both traditional and cumulative images, poses a substantial challenge to the clinical electrophysiologists, who do not have sufficient amount of MRI expertise and experience. The usage of such techniques requires complex decision-making. Making such analysis and decisions, especially in the midst of performing invasive procedures, requires certain knowledge of MR image formation and acquisition principles, which is potentially beyond the achievable for clinical electrophysiologists at present. This can handicap the acceptance of MRI (especially, the intra-procedural one) as a useful aid during clinical EP procedures.

SUMMARY

Embodiments disclosed herein provide systems and methods for automating the acquisition and analysis of contrast enhancement images. Model-free discrimination methods are provided in which discrimination between well-perfused pixels (e.g. normal tissue) and perfusion deficient pixels (e.g. ablation lesions) is automated based on histogram shape. For example, in selected embodiments, discrimination is made based on pixels corresponding to abnormal perfusion (e.g. ablation lesions) and normal perfusion (e.g. normal tissue) form distinctive lobes separated by a minimum formed due to the presence of border pixels. Segmentation of cumulative dynamic contrast enhancement maps by thresholds identified on such histograms is employed to separate abnormally-perfused tissue from the normally-perfused tissue without any user interactions, freeing the user from the necessity to analyze and interpret original dynamic contrast enhancement images or maps derived from them. The histogram properties can also be used for automatic termination of the image acquisition and analysis processes.

Accordingly, in one aspect, there is provided a method of performing contrast-enhanced medical imaging, the method including the steps of: a) prior to injection of a contrast agent to a subject, acquiring one or more baseline images of the subject; b) determining an average baseline image from the one or more baseline images; and after injection of the contrast agent to the subject; c) acquiring a post-injection image;

d) generating at least one cumulative map including image data from previously measured post-injection images, the cumulative map further including a baseline correction based on the average baseline image; e) generating a histogram associated with the cumulative map; f) determining a quantity associated with the shape of the histogram and comparing the quantity to a pre-determined threshold; and g) repeating steps c) to f) until the quantity exceeds the pre-determined threshold.

In another aspect, there is provided a computer implemented method of automating acquisition of dynamic contrast-enhanced medical images, the method including the steps of: a) acquiring baseline image data including one or more baseline images of the subject; b) processing the baseline image data to determine an average baseline image; c) acquiring a post-injection image; d) processing image data from previously measured post-injection images to generate at least one cumulative map and performing a baseline correction based on the average baseline image; e) determining a frequency of occurrence of cumulative map values of pixels within binned intervals in a form suitable for generating a histogram; f) determining a quantity associated with the shape of the histogram and comparing the quantity to a pre-determined threshold; and g) repeating steps c) to f) until the quantity exceeds the pre-determined threshold.

In another aspect, there is provided a computer-readable storage medium comprising instructions for automating acquisition of dynamic contrast-enhanced medical images, wherein execution of the instructions by one or more processors causes the one or more processors to carry out the steps of: a) acquiring baseline image data including one or more baseline images of the subject; b) processing the baseline image data to determine an average baseline image; c) acquiring a post-injection image; d) processing image data from previously measured post-injection images to generate at least one cumulative map and performing a baseline correction based on the average baseline image; e) determining a frequency of occurrence of cumulative map values of pixels within binned intervals in a form suitable for generating a histogram; f) determining a quantity associated with the shape of the histogram and comparing the quantity to a pre-determined threshold; and g) repeating steps c) to f) until the quantity exceeds the pre-determined threshold.

In another aspect, there is provided a method of performing dynamic contrast-enhanced medical imaging, the method including the steps of: a) measuring one or more baseline images of a subject and determining an average baseline image; b) injecting a contrast agent into the subject; c) acquiring a post-injection image; d) generating at least one cumulative map including image data from previously measured post-injection images, the cumulative map further including a baseline correction based on the average baseline image; e) generating a histogram associated with the cumulative map; f) determining a quantity associated with the shape of the histogram and comparing the quantity to a pre-determined threshold; and g) repeating steps c) to f) until the quantity exceeds the pre-determined threshold.

In another aspect, there is provided a method of performing contrast-enhanced medical imaging, the method including the steps of: a) prior to injection of a contrast agent to a subject, acquiring one or more baseline images of the subject; b) determining an average baseline image from the one or more baseline images; and after injection of the contrast agent to the subject; c) acquiring a post-injection image; d) generating at least one cumulative map including image data from previously measured post-injection images, the cumulative map further including a baseline correction based on the average baseline image; and e) correcting for a bias in the cumulative map.

In another aspect, there is provided a computer implemented method of processing dynamic contrast-enhanced medical images, the method including the steps of: a) acquiring baseline image data including one or more baseline images of a subject; b) processing the baseline image data to determine an average baseline image; c) acquiring a post-injection image; d) processing image data from previously measured post-injection images to generate at least one cumulative map and performing a baseline correction based on the average baseline image; and e) processing the cumulative map data and the baseline image data to correct for a bias in the cumulative map.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which.

DETAILED DESCRIPTION

Figure 1:
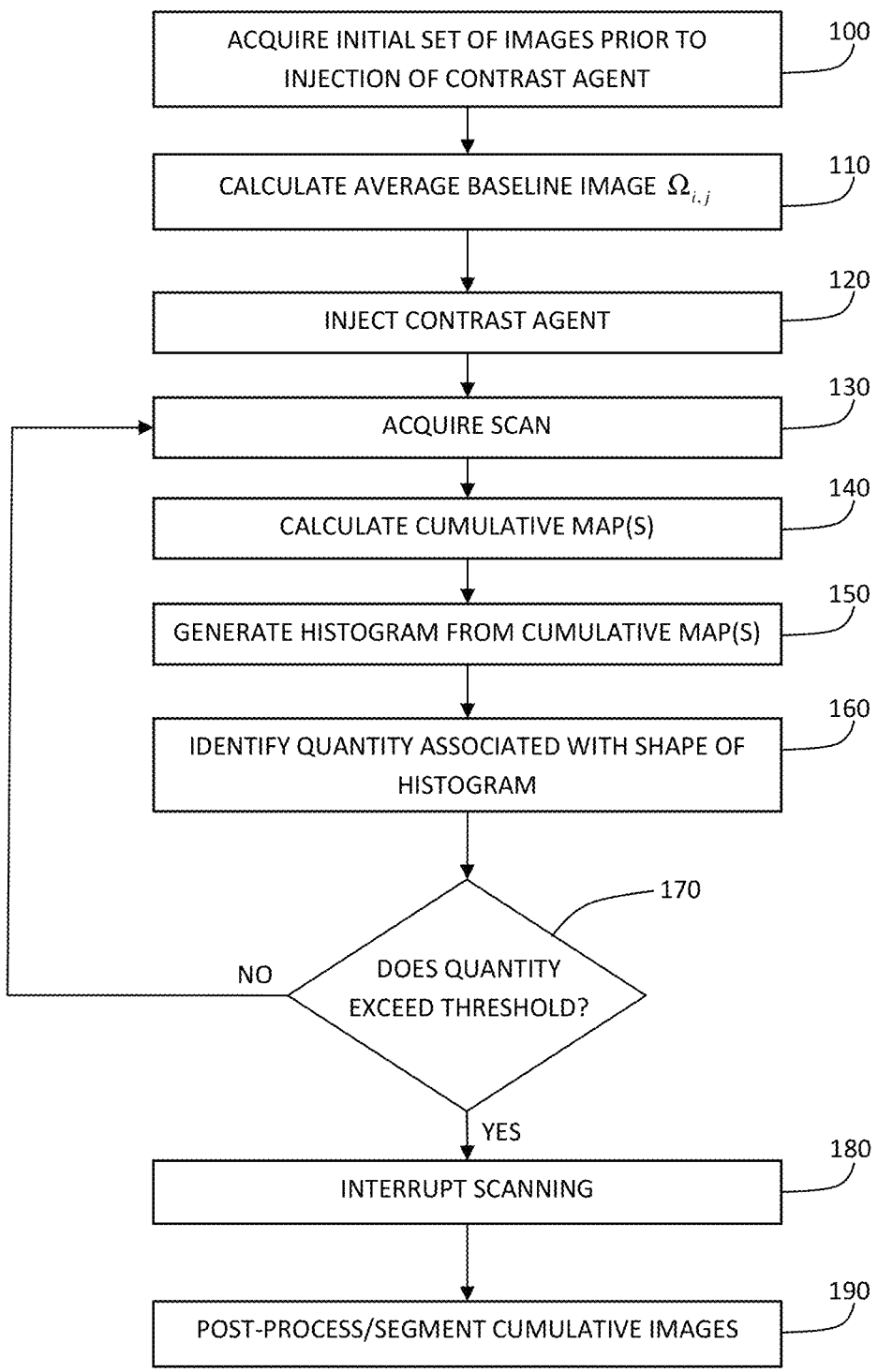
FIG. 1 shows a flow chart for performing automated processing and analysis of cumulative maps according to one embodiment.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately", when used in conjunction with ranges of dimensions of particles, compositions of mixtures or other physical properties or characteristics, are meant to cover slight variations that may exist in the upper and lower limits of the ranges of dimensions so as to not exclude embodiments where on average most of the dimensions are satisfied but where statistically dimensions may exist outside this region. It is not the intention to exclude embodiments such as these from the present disclosure.

Various embodiments, as disclosed below, provide systems and methods for the automated analysis, processing, mapping, and segmentation of cumulative dynamic contrast enhancement medical image data. Selected embodiments automate the interruption of the data acquisition process once a suitable level of visualization or discrimination has been achieved, thus avoiding unnecessary long imaging times. The data obtained during image acquisition may then be used to calculate a dynamic contrast enhancement map associated with the particular acquisition time interval and subsequently perform image segmentation. The described methodology and its benefits may further the acceptance of dynamic contrast enhancement imaging (such as dynamic contrast enhancement imaging MRI) by the clinical electrophysiologists and encourage its applications for intra- and post-operative ablation lesion visualization. Also, the described methodology can be used to differentiate between any areas with different perfusion or washout properties under any circumstances—e.g., tumor neovasculature or residual (after treatment) tumor vs. healthy tissue, ischemic (for any reason) tissue vs. normal tissue, infarcted myocardium or hemorrhagic brain vs. normal ones, cryo or heat ablation lesions, and the like.

According to selected embodiments of the present disclosure, historical or cumulative image data is acquired for a given pixel and processed to determine aspects of the image, as opposed to simply obtaining and processing the instantaneous pixel intensity. As shown below, the differences between cumulative enhancement patterns obtained according to the present embodiments have been found to be more apparent than those between instantaneous enhancement values. In particular, the cumulative dynamic contrast enhancement processing avoids problems associated with signal and noise intermix on noisy dynamic contrast enhancement images, where pixels with different perfusion properties can exhibit similar pixel intensity values and degrade instantaneous images. Accordingly, in selected embodiments, historical information characterizing the dynamic contrast enhancement pattern of a given pixel is accumulated and propagated further (as the data post-processing continues) to be used with any newly acquired data in a computationally efficient manner.

Advantageously, it has been found that methods disclosed herein are suitable for processing datasets that would be deemed to be incomplete according to traditional methods. For example, suitable image contrast and feature segmentation can be achieved, optionally in a fully automated manner, even when images are obtained only during the contrast agent wash-in step and terminated before a global maxima (or minima, or plateau) is obtained.

Moreover, unlike known methods, the dynamic image processing methods disclosed herein do not require a theoretical model of the dynamic contrast enhancement process itself, nor do they require following model-based data fitting to a signal evolution curve with a specific shape. This model-agnostic aspect of the embodiments disclosed herein support the application of the present methods and systems to a wide range of imaging modalities in both clinical and research settings.

In one embodiment, a method is provided for the automated collection and processing of cumulative dynamic contrast enhancement images. In the specific and non-limiting example presently considered, and in the examples provided below, the imaging modality is MRI imaging. It is to be understood that this specific imaging modality is provided merely for heuristic purposes and is not intended to limit the scope of the present disclosure in any way.

Referring to FIG. 1, a flow chart is provided that describes steps involved in performing the present example method. In step 100, an initial set of scanned images are acquired prior to injection of a contrast agent (e.g. a diagnostic contrast agent suitable for generating contrast in acquired medical images). For example, if the imaging modality is MRI, a repetitive MRI scan series (i.e. a "multi-phase" scab) is initiated to acquire an initial image set of the same imaging field of view (FOV) at a number of time instants (i.e. "phases") with appropriate temporal resolution. An appropriate temporal resolution may be achieved, for example, by acquiring one temporal phase with sufficient speed to resolve motion and to generate images substantially free of imaging artifacts. The temporal resolution may also selected to be suitable to depict the course of the contrast agent passage process. In step 110, the average baseline image $\Omega_{i,j}$ is calculated, where i and j are indices representing the different pixels of an acquired two-dimensional image, according to the following equation:

$$\Omega_{i,j} = \frac{1}{n_0} \sum_{k=1}^{n_0} M_{i,j}^k, \qquad [1]$$

where the index k represents each acquired baseline image, $n_o$ is the total number of baseline images that are acquired, and $M_{i,j}^k$ denotes the intensity measured for the (i,j) image pixel in the kth scan.

In one embodiment, this step is performed iteratively in real-time (during the acquisition of images) by calculating, for each scan acquired, the running average baseline image $\Omega_{i,j}$ that is based on only the most recent newly acquired image and the previous value of the average baseline image. In this regard, the calculation of the average need only involve i*j data points, as opposed to $n_o$*i*j data points.

Having obtained a baseline image, the contrast agent is then injected in step 120. Following injection, a series of images are obtained by repeating steps 130-160 to track the cumulative effects of the contrast agent. As shown in the figure, following the acquisition of each new image, a series of image processing steps are carried out in order to determine whether or not sufficient data has been acquired to interrupt the scanning and post-process the image data.

The individual processing steps are now considered in further detail. In step 130, an image is acquired. One or more cumulative maps are then calculated in step 140, where the cumulative maps include both historical image data from previously acquired images, and newly acquired image data from the present scan. When performing step 140 for the first time, there is no historical image data, and the cumulative maps are calculated based on the presently acquired image data alone.

In one example implementation, the cumulative maps may be one or more of the following two dimensionless cumulative maps: the cumulative intensity difference (CID), defined as:

$$\Psi_{i,j}^n = \frac{1}{\nu} \sum_{k=n_0+1}^{n} (M_{i,j}^k - \Omega_{i,j}), \qquad [2]$$

and the cumulative intensity ratio (CIR), defined as $$\Phi_{i,j}^n = \sum_{k=n_0+1}^{n} \frac{M_{i,j}^k}{\Omega_{i,j}} \ \forall \ (i, j) : \Omega_{i,j} \neq 0, \qquad [3]$$

where n is the total number of images acquired. As shown in equation 2, the CID may be normalized and made dimensionless by dividing by the average baseline intensity $\nu$:

$$\nu = \frac{1}{I \times J} \sum_{i=1}^{I} \sum_{j=1}^{J} \Omega_{i,j}, \qquad [4]$$

where $\nu$ is obtained by averaging $\Omega_{i,j}$ over all pixels to serve as a convenient normalization constant.

The CID cumulative map therefore provides a cumulative measure of the intensity difference between images data $M_{i,j}^k$ obtained following the injection of contrast agent and the average baseline image $\Omega_{i,j}$. Similarly, the CIR cumulative map provides a cumulative measure of the intensity ratio between images data $M_{i,j}^k$ obtained following the injection of contrast agent and the average baseline image $\Omega_{i,j}$. It is to be understood that these cumulative maps are only provided as examples, and that various related cumulative maps may be constructed without departing from the scope of the present embodiment.

While $\Psi_{i,j}^n$ and $\Phi_{i,j}^n$ are dimensionless and provide the same type of information, they differ by their dynamic range and sensitivity to noise due to the different normalization factors. They can be analyzed separately, or, in other embodiments, combined into a single map. In one example implementation, the CID and CIR may be normalized to the dynamic range of [0;1] and summed to form a cumulative enhancement sum (CES):

$$\Lambda_{i,j}^n = \frac{\Psi_{i,j}^n - \text{MIN}(\Psi^n)}{\text{MAX}(\Psi^n) - \text{MIN}(\Psi^n)} + \frac{\Phi_{i,j}^n - \text{MIN}(\Phi^n)}{\text{MAX}(\Phi^n) - \text{MIN}(\Phi^n)}, \qquad [5]$$

where MIN( ) and MAX( ) denote the minimal and maximal pixel values of the corresponding map as a whole one identified prior to performing any other operations on it.

It is to be understood that equation 5 provides only one example implementation of a cumulative map based on both a cumulative intensity difference and a cumulative intensity ratio. In other examples, the sum can involve direct arithmetical addition, adding squared quantities (with or without a square root operation), adding logarithms or roots, and the like. If deemed suitable, the normalization step can be omitted.

In one embodiment, the calculation of the one or more cumulative maps is performed iteratively in real-time (during the acquisition of images) by calculating, for each scan acquired, an updated value that is based on only the most recent newly acquired image and the previous value of the cumulative map. In this regard, the calculation of the cumulative map, when performing step 140, need only involve i*j data points, as opposed to (n−n$_o$)*i*j data points.

Having obtained the one or more cumulative maps in step 140, one or more of the cumulative maps is processed in step 150 to generate a histogram describing the frequency of occurrence of different values of the cumulative map (within binned intervals) among the various pixels.

Figure 2:
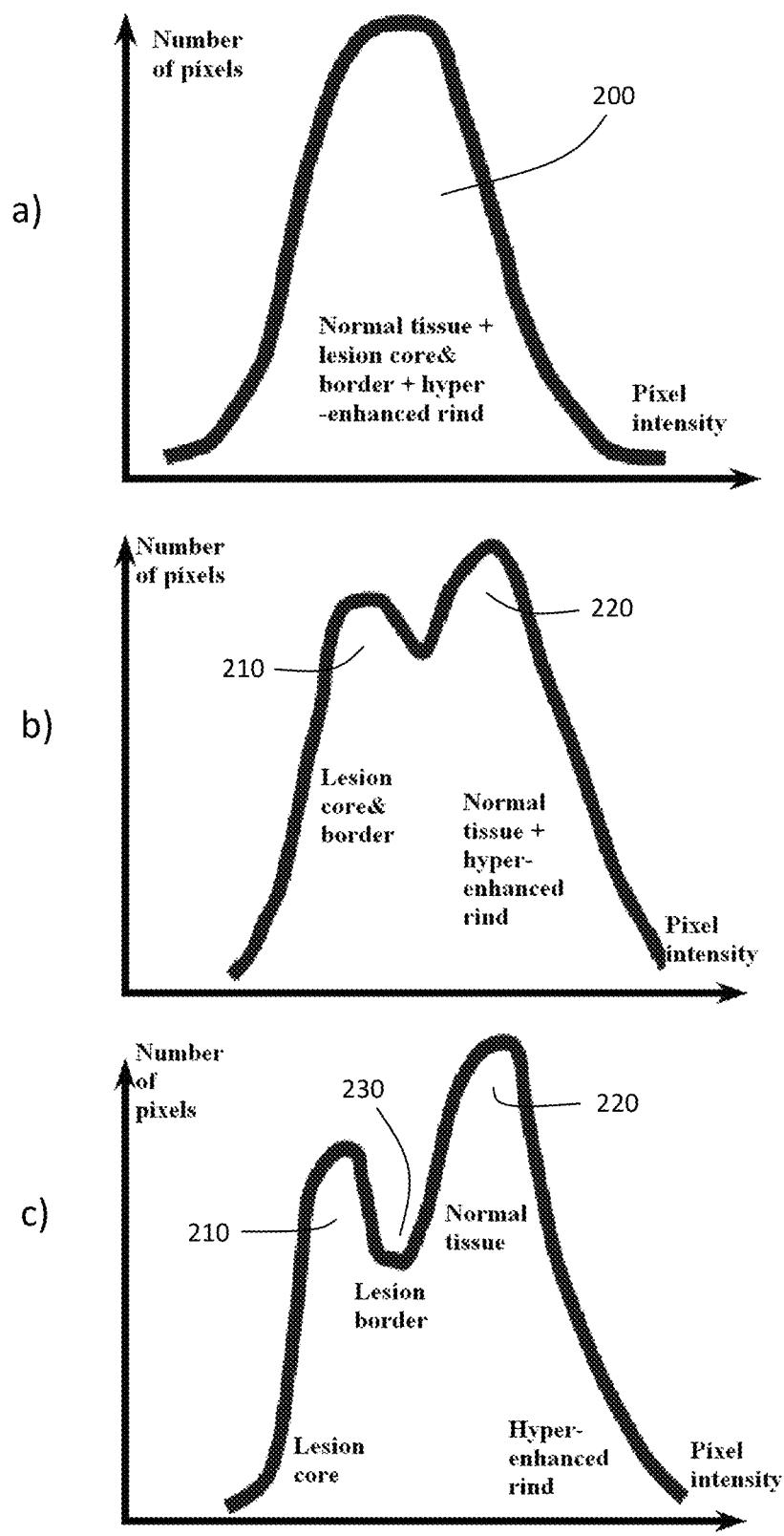
FIG. 2 is a sketch depicting evolution of a typical CES map histogram from the beginning of data acquisition and analysis, through its (a) early, (b) middle and (c) later stages.

In one embodiment, as illustrated in FIG. 2, when the field of view of the image includes tissues having different perfusion rates of the contrast agent, the histogram shape evolves as more post-injection images are acquired (which are used to calculate more cumulative enhancement maps), and a characteristic shape emerges. This characteristic shape may then be employed to identify a point in time, or a number of acquired images, for which sufficient a signal-to-noise ratio and/or contrast-to-noise ratio is obtained for subsequent post-processing.

FIG. 2 illustrates an example of the CES histogram (obtained by calculating the CES according to equation 5), and its evolution under cumulative dynamic contrast enhanced imaging of a field of view including an ablated tissue region. Initially, a single lobe 200 is observed in the CES map histogram during the early wash-in period, as seen in FIG. 2(a). However, as additional contrast agent is absorbed and the CES cumulative image is further amended by additional images, the width of the histogram increases, and the histogram develops additional structure, such as lobes 210 and 220 shown in FIG. 2(b).

This change in the histogram profile occurs because the core region of the ablated tissue exhibits a perfusion rate that is, for example, considerably lower (or zero) relative to that of the surrounding non-ablated tissue. As the CES map histogram further evolves in time, a local minimum 230 is formed between the two lobes as further image contrast is achieved, as shown in FIG. 2(c). This contrast between the ablation lesion cores, borders and normal tissue arises due to the normalization and summation typical for the cumulative characteristics (see equations 2, 3, and 5), so it will improve as the number of acquired images (n) grows. As the lesion conspicuousness on the CES (or, for example, CID or CIS) maps improves with each newly acquired dynamic contrast enhancement image, this will result in a characteristic evolution of the shapes of their histograms.

Figure 3:
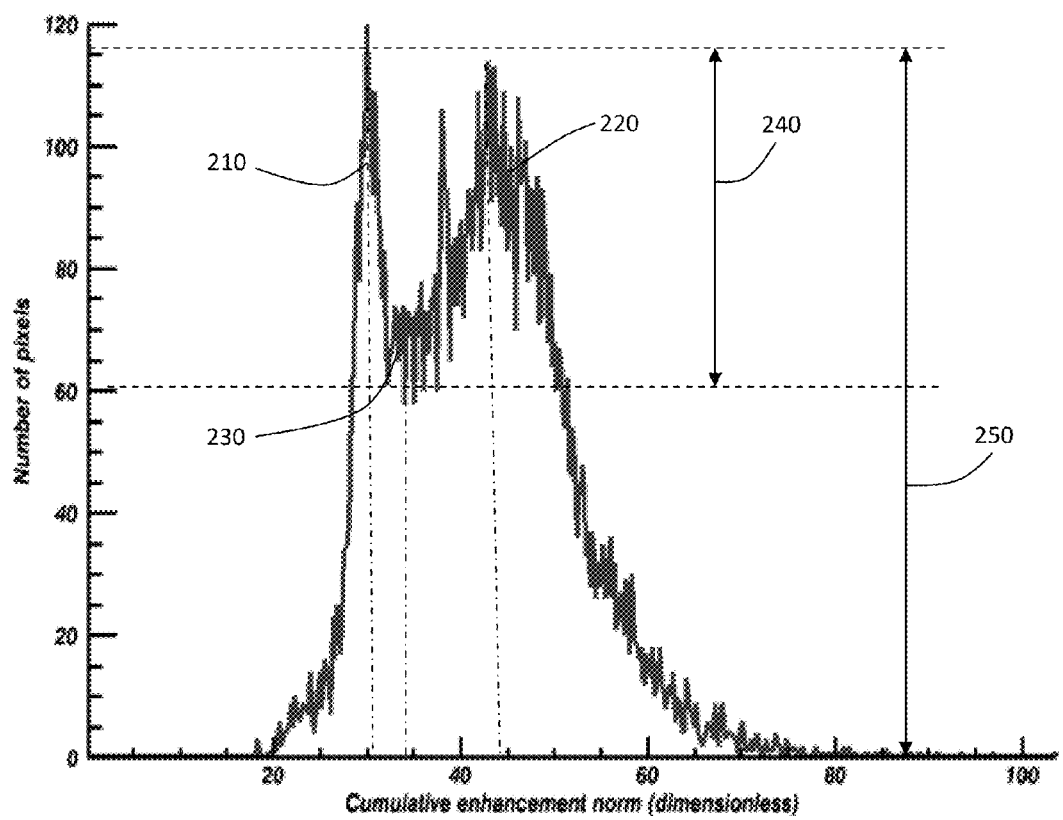
FIG. 3 shows the identification of features on the histogram for comparison with a threshold for automated scan termination.

Referring again to FIG. 1, having generated the histogram, one or more characteristic quantities associated with the shape of the histogram are then identified in step 160. FIG. 3 illustrates the identification of the features in the histogram for the determination of a characteristic quantity. In one example implementation, the quantity is formed as the ratio between the peak-valley offset 240 and the peak height 250. In another embodiment, the quantity may be formed by comparing not only the peak values, but also the peak positions. When determining the peak height, it may be beneficial to average the two maximum peak values.

The quantity may be determined by automated analysis of the histogram. For example, an algorithm may be performed to determine the positions and values of the histogram maxima and local minimum by comparing the different binned values.

It is to be understood that many other suitable measured of the histogram shape could also or alternatively be employed. For example, with regard to the histogram shape shown in FIG. 3, other suitable example measures include the x-axis separation between the peaks and the full-width half-maximum of the composite double-lobe structure. The full-width half-maximum measure may be well suited to implementations in which the separation between peaks is insufficient to produce a sufficiently depressed local minimum. In other embodiments, one or more quantities associated with the shape of the histogram may be obtained by fitting the histogram to a pre-determined functional form. For example, the positions of the peaks 210 and 220, and their corresponding full-width half-maxima, may be obtained mathematically by fitting the histogram to a double Gaussian function using a least-squares fitting routine. In another example, a parabolic curve may be fit to the histogram minimum and two maxima. In this example, three points may be sufficient to calculate fitting coefficients according to the functional form $a*x^2+b*x+c=0$. These fitting coefficients (a, b and c) describe a particular shape, which will be becoming more deep and wide as the cumulative maps evolve in the present example.

As shown in step 170 of FIG. 1, the quantity may then be compared with a threshold value in order to determine whether or not to continue acquiring additional images. The threshold may be a value of the quantity beyond which (or alternatively below which) a sufficient signal-to-noise ratio is obtained for subsequent image processing (such as image segmentation). The value of the threshold may be experimentally determined through a calibration process. Step 170 may involve comparing a single quantity with a single threshold, or may involve the comparison of two or more quantities with their associated thresholds.

The method provided above describes the automatic interruption of image acquisition based on the processing of a histogram associated with a cumulative map. Accordingly, in some embodiments, image acquisition may be interrupted based on the processing of one cumulative map. If the imaging involves the acquisition of multiple image slices (i.e. image planes), then one or more cumulative maps may be selected for processing according to the aforementioned method. In one example implementation, a particular image slice may be selected for processing, such as an image slice located in a pre-determined anatomical location. In another example, a particular image slice for processing may be selectable by a user.

In another example implementation, two or more image slices may be selected for processing to determine when image acquisition may be interrupted. The two or more image slices may be selected according to various criteria. Non-limiting examples of selecting the slices include selecting the slices according to a pre-selected spatial distribution, a pre-determined spatial interval, prescribed anatomical locations, or at random.

When processing the cumulative maps corresponding to the two or more image slices, different methods may be employed to determine when the acquisition of images may be interrupted. In one example implementation, the determination may be made once a quantity associated with a shape of a histogram corresponding to a cumulative map of one or more of the image slices exceeds a threshold. In another embodiment, the histograms associated with the per-slice cumulative maps of two or more image slices may be processed to determine a composite quantity for comparison to a threshold. The threshold may be an array of per-slice thresholds, or a single threshold that is compared to a quantity based on multiple per-slice quantities. For example, the quantities associated with each of the histograms may be averaged to produce an average quantity. In another example, weighting factors may be applied when averaging the quantities, according to a pre-determined set of weights. For example, weights may be selected based on treatment result assessment, with the slices having the most importance receiving the highest weights, and the slices with the least importance receiving the lowest weights. In one embodiment, the two or more slices could be selected to be clinically important slices, and the quantities associated with each clinically important slice could be combined according to "importance coefficients".

If the characteristic histogram shape evolution is not observed (for example, the histogram remains mono-lobal, which may occur if the separation between abnormal tissue and normal tissue on the cumulative enhancement maps is weak), the acquisition and analysis of the dynamic contrast enhancement images continues as illustrated by FIG. 1 (the backward loop between steps 170 and 130). In case the desired histogram shape has not been reached until the end of the dynamic scan (i.e. until the last temporal phase of the current dynamic contrast enhancement scan has been acquired), then the last calculated cumulative enhancement map may be segmented to obtain the representation of the ablation lesions. In another embodiment, the histogram shape may be smoothed prior to performing histogram shape analysis and threshold comparison.

If the quantity associated with the histogram shape does not exceed the threshold, then an additional scan is acquired and processed by repeating steps 130-160. If, however, the quantity determined in the above step exceeds the threshold, then the scanning process may be interrupted. In one example implementation, the interruption of the scanning may be performed automatically, for example, in response to a control signal communicated from the processor to the imaging device. Alternatively, an indication may be communicated to the user that sufficient data has been obtained such that the scanning scan may be interrupted by the user. Suitable indications include textual or audible indications, such as an audible sound indicating the collection of sufficient imaging data.

Although the present embodiment is described and illustrated herein in terms of the graphical generation of a histogram, it is to be understood that the disclosed graphical analysis is merely one example implementation of the present method step. It is to be understood that the steps of generating and processing the histogram may be performed by a processor, where the processor is employed to process and/or reformat the cumulative map data into a tabular representation in which the frequency of cumulative map values are determined within binned intervals, and where the processor is employed to obtain or extract, from the tabular representation, one or more characteristic quantities associated with a corresponding histogram shape.

After having interrupted the acquisition of images in step 180, the cumulative image data, obtained in the form of one or more cumulative maps, may be processed for image analysis. The subsequent image processing step may be fully automated and performed by the processor performing the above analysis steps, or may be performed off-line on a separate computing system.

In one embodiment, the one or more cumulative maps may be segmented to determine a border between tissue regions having different perfusion characteristics. For example, the characteristic histogram shape identified as described above can be utilized for automated segmentation without the need to user input or interaction. The segmentation process may be performed by selecting, as a location for the segmentation threshold, the local minimum in between the two peaks on the cumulative map, such that pixels with cumulative map values exceeding the cumulative map value corresponding to the local minimum are deemed as being associated with one type of tissue (e.g. normal tissue) and all pixels with cumulative map values less than the cumulative map value corresponding to the local minimum are deemed as being associated with another type of tissue (e.g. ablated tissue or tissue having a pathology).

In another embodiment, segmentation may be performed by the Otsu method (25). After having performed segmentation, the resulting cumulative map may be enhanced by one or more of erosion and dilation, for example, by a single passage of an 8-connectivity element (26) followed by low-pass filtering using a single passage of a 3×3 pixel averaging filter.

Although the preceding embodiments describe segmentation by the Otsu method or via thresholding, it is to be understood that any suitable segmentation method may be implemented. Segmentation may be performed on the temporal series of the cumulative map. In one example, a clustering method such as the fuzzy C-means method may be employed.

The aforementioned automated scanning, processing, interruption, and optional post-processing methods may be beneficial in providing to a clinician (e.g. a clinical electrophysiologist), in real-time, processed and optionally segmented dynamic contrast enhancement images. This may be a significant benefit to clinical workflow and speed in making decisions concerning ablation, lesion delineation, and the potential success of a medical procedure.

In another embodiment, the aforementioned methods of calculating cumulative maps may be improved by correcting for the presence of bias terms. The presence of the bias terms, and their removal and/or cancellation, is henceforth described with reference to an example mathematical description of the various sources of signals when performing imaging measurements.

Mathematically, it can be shown that the magnitude of the image intensity $M_{i,j}^k$ of each pixel can be approximated by a sum of signal-dominated and noise-dominated terms (Appendix 1, [21-23]), while the signal-dominated term can be considered as a sum of CE-independent and CE-caused terms (Appendix 2, 24):

$$M_{i,j}(t=t_k)=M_{i,j}^k=\beta_{i,j}+\xi_{i,j}^k+\chi_{i,j}^k \qquad [6],$$

where $i=1, \ldots, I$ and $j=1, \ldots, J$ denote the pixel's position within a region of interest (ROI) of the size I×J pixels; k denotes the number of a dynamic phase acquired at the time $t_k$ as counted from the onset of the image acquisition procedure; $\beta_{i,j}$ denotes the signal intensity contribution due to the inherent properties of the biological tissues inside the imaged pixel (i.e., the signal-dominated term); $\xi_{i,j}^k$ and $\chi_{i,j}^k$ denote signal intensity contributions due to the time-transient contrast agent content and noise-dominated term correspondingly. If $\beta_{i,j}+\xi_{i,j}^k>\chi_{i,j}^k$, $\chi_{i,j}^k$ has zero mean and can take both positive and negative values (Appendix 1).

As noted above, during image acquisition, the first $n_0$ images ($k=1, 2, \ldots, n_0$) are acquired prior to contrast agent injection for the purpose of obtaining an averaged baseline image, such that:

$$\xi_{i,j}^k=0 \forall k \leq n_0 \qquad [7].$$

The contrast agent-free images can be averaged to form the pre-injection baseline image $\Omega_{i,j}$, as shown above in equation 1:

$$\Omega_{i,j} = \frac{1}{n_0}\sum_{k=1}^{n_0} M_{i,j}^k = \beta_{i,j} + \frac{1}{n_0}\sum_{k=1}^{n_0} \chi_{i,j}^k, \qquad [8]$$

The mean signal intensity of the baseline image can be obtained by averaging over all pixels to serve as a convenient normalization constant:

$$v = \frac{1}{I \times J} \sum_{i=1}^{I} \sum_{j=1}^{J} \Omega_{i,j} = \quad [9]$$

$$\frac{1}{I \times J} \sum_{i=1}^{I} \sum_{j=1}^{J} \beta_{i,j} + \frac{1}{n_0 \times I \times J} \sum_{k=1}^{n_0} \sum_{i=1}^{I} \sum_{j=1}^{J} \chi_{i,j}^{k} \approx \frac{1}{I \times J} \sum_{i=1}^{I} \sum_{j=1}^{J} \beta_{i,j}.$$

As contrast agent injection starts at the time of the acquisition of the $n_0+1$-th image, the pixels occupied by perfused tissues will gain addition signal intensities $\xi_{i,j}^m$ on the rest of the images. The total signal enhancement (if any) gained by a pixel after contrast agent injection at the time $t_n$ can be estimated using cumulative intensity difference (CID) as well as the cumulative intensity ratio (CIR) defined in equations 2 and 3, respectively.

Substituting $M_{i,j}^k$ and $\Omega_{i,j}$ in equations 2 and 3 with equations 6 and 8 correspondingly:

$$\Psi_{i,j}^n = \frac{1}{v} \sum_{k=n_0+1}^{n} \xi_{i,j}^k + \frac{1}{v} \sum_{k=n_0+1}^{n} \chi_{i,j}^k - \frac{(n-n_0)}{v \times n_0} \sum_{k'=1}^{n_0} \chi_{i,j}^{k'} \quad [10]$$

and $$\Phi_{i,j}^n = (n-n_0) + \frac{1}{\Omega_{i,j}} \sum_{k=n_0+1}^{n} \xi_{i,j}^k + \frac{1}{\Omega_{i,j}} \sum_{k=n_0+1}^{n} \chi_{i,j}^k - \frac{(n-n_0)}{\Omega_{i,j} \times n_0} \sum_{k'=1}^{n_0} \chi_{i,j}^{k'}. \quad [11]$$

The linearly growing bias $(n-n_0)$ can be eliminated from the CIR map by subtraction:

$$\Phi_{i,j}^n - (n-n_0) = \sum_{k=n_0+1}^{n} \frac{M_{i,j}^k}{\Omega_{i,j}} - n + n_0. \quad [12]$$

Both CID and CIR are biased by the last terms proportional to $$\frac{1}{n_0} \sum_{k'=1}^{n_0} \chi_{i,j}^{k'},$$

which can be estimated from the baseline image if $n_0$ is large enough:

$$\Theta = \frac{1}{n_0} \sum_{k'=1}^{n_0} (M_{i,j}^{k'} - \Omega_{i,j}) \approx \frac{1}{n_0} \sum_{k'=1}^{n_0} \chi_{i,j}^{k'}. \quad [13]$$

In this case, the corrected CID and CID maps can be calculated as $$\Psi_{i,j}^n = \frac{1}{v} \sum_{k=n_0+1}^{n} (M_{i,j}^k - \Omega_{i,j}) + \frac{(n-n_0)}{v} \Theta = \frac{1}{v} \sum_{k=n_0+1}^{n} (M_{i,j}^k - \Omega_{i,j} + \Theta), \quad [14]$$

$$\Phi_{i,j}^n = \sum_{k=n_0+1}^{n} \frac{M_{i,j}^k}{\Omega_{i,j}} - (n-n_0) + \frac{(n-n_0)}{\Omega_{i,j}} \Theta = \quad [15]$$

$$\frac{1}{\Omega_{i,j}} \sum_{k=n_0+1}^{n} (M_{i,j}^k + \Theta) - (n-n_0)$$

to deliver the following estimates:

$$\tilde{\Psi}_{i,j}^n \approx \frac{1}{v} \sum_{k=n_0+1}^{n} \xi_{i,j}^k + \frac{1}{v} \sum_{k=n_0+1}^{n} \chi_{i,j}^k \quad [16]$$

and $$\tilde{\Phi}_{i,j}^n \approx \frac{1}{\Omega_{i,j}} \sum_{k=n_0+1}^{n} \xi_{i,j}^k + \frac{1}{\Omega_{i,j}} \sum_{k=n_0+1}^{n} \chi_{i,j}^k. \quad [17]$$

Equations 8, 4 and 13 can be evaluated as soon as the first $n_0$ images have been acquired (or even during the acquisition of the first $n_0$ images. During the rest of the dynamic contrast enhancement scan, $\tilde{\Psi}_{i,j}^n$ and $\tilde{\Phi}_{i,j}^n$ can be calculated iteratively in real time according to equations 14 and 15 correspondingly using only the images acquired up to (and including) the current time instant without any model-based curve fitting, so the image acquisition and analysis processes can be stopped at any moment. Furthermore, the CES, including a correction for bias, can be obtained by substituting $\tilde{\Psi}_{i,j}^n$ and $\tilde{\Phi}_{i,j}^n$ into equation 5.

The first terms in equations 16 and 17 contain summation of the CE signal contributions ($\xi_{i,j}^k$) and will approach zero for the non-perfused pixels, while they will have higher values for the perfused pixels and reach their maximum for the pixels constituting the hyper-enhanced ablation lesion rim.

The second terms equations 16 and 17 contain summation of the noise-dominated terms ($\chi_{i,j}^k$). For pixels exhibiting a sufficiently strong image signal (for whom the signal-dominated term is larger than the noise dominated-one), the sum will approach zero since the positive and negative summation terms will mutually annihilate. Otherwise, it will approach a positive constant dependent on the statistical properties of the original image acquisition noise.

Thus, when $n_0$ and $n$ are large, the dynamic range of the cumulative enhancement maps calculated according equations 14 and 15 will be defined by the lesion core $$\left(\text{both} \sum_{k=n_0+1}^{n} \xi_{i,j}^k \to 0 \text{ and } \sum_{k=n_0+1}^{n} \chi_{i,j}^k \to 0\right)$$

and hyper-enhanced ablation lesions rims $$\left(\text{maximum} \sum_{k=n_0+1}^{n} \xi_{i,j}^k \text{ while } \sum_{k=n_0+1}^{n} \chi_{i,j}^k \to 0\right).$$

The pixels containing no tissue will have intensities slightly higher than the lesion core $$\left(\sum_{k=n_0+1}^{n} \xi_{i,j}^n \to 0 \text{ and } \sum_{k=n_0+1}^{n} \chi_{i,j}^k \to const > 0\right),$$

while the pixels containing normal perfused tissue will occupy the rest of the dynamic range depending on their perfusion state and ability to retain the contrast agent $$\left(\text{intermediate} \sum_{k=n_0+1}^{n} \xi_{i,j}^k \text{ while } \sum_{k=n_0+1}^{n} \chi_{i,j}^k \to 0\right).$$

The ablation lesion core visibility can be enhanced even more by excluding from further ($n \ge n_0+1$) calculations the empty pixels, which demonstrate too low baseline signal $\Omega_{i,j}$. Since the described method operates on the signal intensity time series of each pixel separately, it does not affect the spatial resolution of the original data set. It only improves the contrast between pixels with different dynamic contrast enhancement properties without reducing the spatial resolution of the original data set.

While the preceding example has provided methods for correcting for the presence of bias in selected cumulative maps (namely the CID, CIR and CES cumulative maps), the bias correction embodiment disclosed herein is not intended to be limited to those specific cumulative maps. It is to be understood that the bias correction methods disclosed herein may be adapted and/or applied to a wide range of cumulative maps based on the preceding disclosure.

Figure 4:
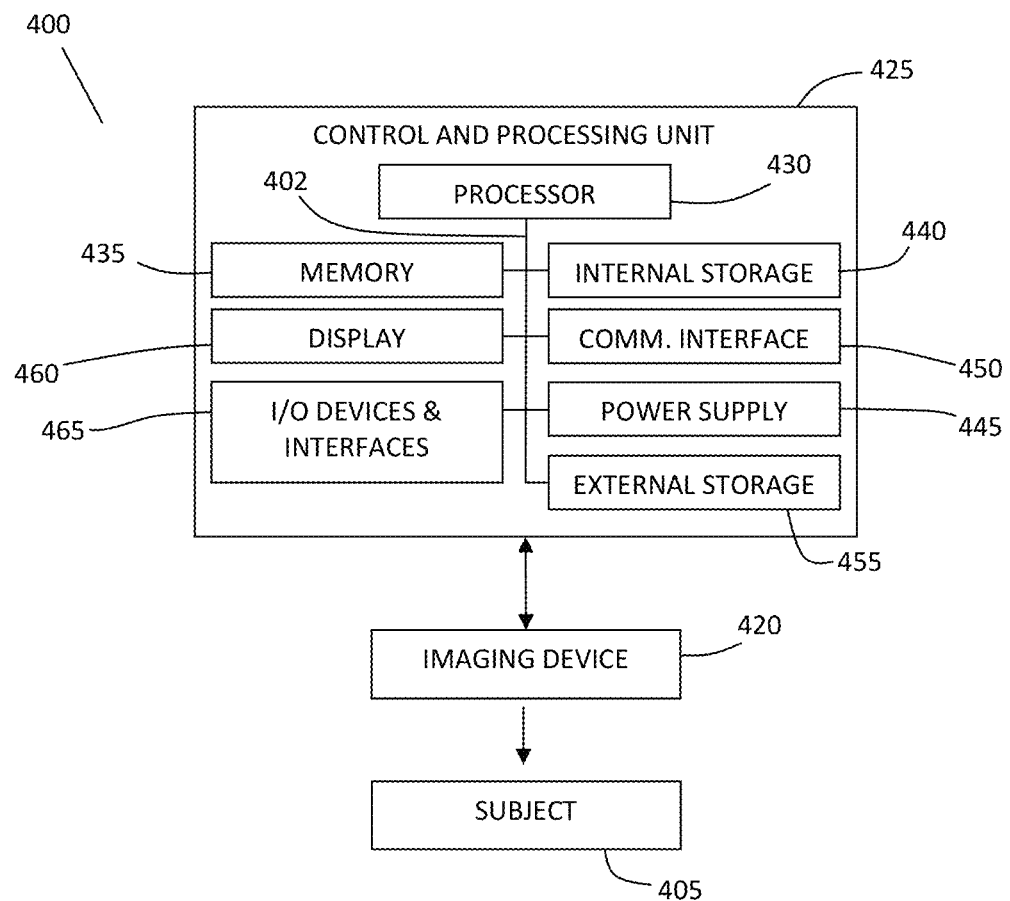
FIG. 4 is a schematic of a system for performing automated cumulative dynamic enhancement imaging measurements.

Referring now to FIG. 4, an example system 400 for performing the aforementioned methods is illustrated. System 400 includes imaging device 420 and control and processing unit 425, the latter of which is described in further detail below.

Imaging device 425 obtains images of subject 405 within a prescribed field of view. Imaging device 425 may be any medical imaging device suitable for performing cumulative dynamic contrast enhanced imaging. A non-limiting list of example imaging devices includes MRI, CT, US, X-Ray, PET, SPECT, nuclear perfusion modalities and optical modalities.

Control and processing unit 425 may be interfaced with imaging device for the receiving acquired images, and optionally for controlling the acquisition of images. Control and processing unit 425 receives image data from imaging device 420 and processes the imaging data as per the aforementioned methods. In some embodiments, control and processing unit 425 is configured to actively control aspects of imaging device 420, such as the interruption of a scan after having determined that a quantity associated with a cumulative map histogram exceeds a pre-defined threshold, as described above.

Some aspects of the present disclosure can be embodied, at least in part, in software. That is, the techniques can be carried out in a computer system or other data processing system in response to its processor, such as a microprocessor, executing sequences of instructions contained in a memory, such as ROM, volatile RAM, non-volatile memory, cache, magnetic and optical disks, or a remote storage device. Further, the instructions can be downloaded into a computing device over a data network in a form of compiled and linked version. Alternatively, the logic to perform the processes as discussed above could be implemented in additional computer and/or machine readable media, such as discrete hardware components as large-scale integrated circuits (LSI's), application-specific integrated circuits (ASIC's), or firmware such as electrically erasable programmable read-only memory (EEPROM's).

FIG. 4 provides an example implementation of control and processing unit 425, which includes one or more processors 430 (for example, a CPU/microprocessor), bus 402, memory 435, which may include random access memory (RAM) and/or read only memory (ROM), one or more internal storage devices 440 (e.g. a hard disk drive, compact disk drive or internal flash memory), a power supply 445, one more communications interfaces 450, external storage 455, a display 460 and various input/output devices and/or interfaces 455 (e.g., a receiver, a transmitter, a speaker, a display, an imaging sensor, such as those used in a digital still camera or digital video camera, a clock, an output port, a user input device, such as a keyboard, a keypad, a mouse, a position tracked stylus, a position tracked probe, a foot switch, and/or a microphone for capturing speech commands).

Although only one of each component is illustrated in FIG. 4, any number of each component can be included control and processing unit 400. For example, a computer typically contains a number of different data storage media. Furthermore, although bus 402 is depicted as a single connection between all of the components, it will be appreciated that the bus 402 may represent one or more circuits, devices or communication channels which link two or more of the components. For example, in personal computers, bus 402 often includes or is a motherboard.

In one embodiment, control and processing unit 425 may be, or include, a general purpose computer or any other hardware equivalents. Control and processing unit 425 may also be implemented as one or more physical devices that are coupled to processor 430 through one of more communications channels or interfaces. For example, control and processing unit 425 can be implemented using application specific integrated circuits (ASIC). Alternatively, control and processing unit 425 can be implemented as a combination of hardware and software, where the software is loaded into the processor from the memory or over a network connection.

Control and processing unit 425 may be programmed with a set of instructions which when executed in the processor causes the system to perform one or more methods described in the disclosure. Control and processing unit 425 may include many more or less components than those shown.

While some embodiments have been described in the context of fully functioning computers and computer systems, those skilled in the art will appreciate that various embodiments are capable of being distributed as a program product in a variety of forms and are capable of being applied regardless of the particular type of machine or computer readable media used to actually effect the distribution.

A computer readable medium can be used to store software and data which when executed by a data processing system causes the system to perform various methods. The executable software and data can be stored in various places including for example ROM, volatile RAM, non-volatile memory and/or cache. Portions of this software and/or data can be stored in any one of these storage devices. In general, a machine readable medium includes any mechanism that provides (i.e., stores and/or transmits) information in a form accessible by a machine (e.g., a computer, network device, personal digital assistant, manufacturing tool, any device with a set of one or more processors, etc.).

Examples of computer-readable media include but are not limited to recordable and non-recordable type media such as volatile and non-volatile memory devices, read only memory (ROM), random access memory (RAM), flash memory devices, floppy and other removable disks, magnetic disk storage media, optical storage media (e.g., compact discs (CDs), digital versatile disks (DVDs), etc.), among others. The instructions can be embodied in digital and analog communication links for electrical, optical, acoustical or other forms of propagated signals, such as carrier waves, infrared signals, digital signals, and the like.

The proposed cumulative method has several advantages as compared to known image processing protocols. In particular, the present methods are well suited to the processing of noisy images showing no global minima, maxima or plateau, to which the traditional concepts (such as mean time to enhance, time to peak or minimum) are not applicable. Furthermore, embodiments provided herein are resistant to image acquisition noise, as shown in the examples below. In addition, the present methods do not affect the spatial resolution of the original images, since it operates in the temporal domain only on a pixel-by-pixel basis. Although pre-filtering of the input data may improve the quality of the resulting cumulative maps, the methods provided herein can generally perform without pre-filtering while delivering satisfactory lesion visualization.

In addition, the methods described herein do not employ or require any models of the enhancement pattern, and can be implemented without curve fitting. The methods advantageously depict ablation lesions, pathological tissue, or other abnormalities associated with spatially varied perfusion rates at any moment during the dynamic contrast enhancement data acquisition process, starting at a very short time after contrast agent injection (even in the cases when the original contrast enhanced curves have little or no distinctive shape). The calculations employed in the aforementioned methods may be performed iteratively and take very little time (as compared to the dynamic acquisition time), and all data processing can be executed in real time in parallel with data acquisition and optional automated interruption.

Clinical applications of the aforementioned methods on moving anatomies may benefit from motion compensation during the image acquisition for example cardiac and/or respiratory gating (the latter may be performed using either respiratory belts or navigator echo or their combination (27)). The present methods are not more vulnerable to motion than any other existing dynamic contrast enhancement data analysis approaches. However, the ability of the method to generate proper lesion visualization shortly after contrast agent injection without any additional requirements to sample a particular CE pattern is expected to render the method less vulnerable to gross anatomy displacement resulting from patient motion. If such displacement occurs, the data acquired before it may be sufficient to achieve proper lesion visualization.

While the cumulative map processing methods described above, and demonstrated in the forthcoming examples, have been disclosed as applied to MRI imaging methods, it is to be understood that the embodiments provided in the present disclosure are not intended to be limited only to MRI dynamic contrast enhancement images.

The examples described below, the present methods are applied to the dynamic contrast imaging of ablated tissue. In other example implementations, the methods may be applied to the processing of dynamic data of other contrasts, such as, but not limited to, images (such as T2w images) depicting stem cell injection, and images showing a distribution of holmium microspheres evolving in real time.

The techniques described above can be applied towards disease detection or other diagnostic procedures in other organs and tissues in the body, based on their characteristic vascularization, such as muscles, liver, kidney, brain. In other examples, bone density, bone integrity and fracture detection can be determined using the present imaging techniques. Other potential applications of the methodologies disclosed above include detection and treatment of tumors (due to overvascularization) and localization of scars (due to under vascularization), detection of any diseases characterized by perfusion such as early stroke, early pulmonary aneurysm and myocardial infarcts.

Any biological, biocompatible and/or non-biological materials that have the potential of vascularization or perfusion, possess an open microstructure and/or porosity, can be successfully visualized using this technique for structural, anatomical, physiological, and/or functional assessment.

Other examples of contrast imaging modalities that can be improved using this methodology include CT, US, X-Ray, PET, SPECT, nuclear perfusion modality and optical modalities.

The following examples are presented to enable those skilled in the art to understand and to practice embodiments of the present disclosure. They should not be considered as a limitation on the scope of the present embodiments, but merely as being illustrative and representative thereof.

EXAMPLES

Example 1

Experimental Demonstration of Cumulative Dynamic Contrast Enhancement Mapping

The present example describes an experimental realization and demonstration of selected embodiments of the disclosure.

Using clinical EP catheters, 56 RF lesions were created in the *Latissimus dorsi* muscles of 15 rabbits with power and time settings varying in the range 30-35 Watt/30-45 sec. MRI was performed on a 1.5 T Signa HD scanner (General Electric Healthcare) using dynamic contrast enhancement as well as T2w, SSFP and Delayed Enhancement (DE) scans for comparison. Sedated animals were positioned inside a standard transmit-receive birdcage head coil. MR imaging sessions lasted ~2.5-3 hrs. and were performed after the ablations as follows: at few minutes (4 rabbits), ~3 hours (11 rabbits), ~1 week (2 rabbits), ~2 weeks (5 rabbits), and ~4 weeks (4 rabbits) after the ablations.

3D T2w and SSFP imaging was performed before contrast agent injection using Fast Spin Echo (FSE) and FIESTA correspondingly. 3D DE imaging was performed using Inversion Recovery Fast RF-Spoiled Gradient Echo (IR-FSPGR). Two 3D sets of IR-FSPGR images were acquired per imaging session—before contrast agent injection and 5-9 min. after injection. In some cases, pre-contrast agent 3D IR-FSPGR data sets were subtracted from the corresponding post-contrast agent data sets for better background signal suppression. Dynamic contrast enhancement images were acquired using 2D multi-phase FSPGR. Typically, animals were injected with either 0.05 ml/kg of Gadovist or 0.1 ml/kg of Gadoteridol and injections started as soon as 2-5 pre-contrast agent baseline phases have been acquired. The contrast agent injection process lasted a few seconds.

Different MR image acquisition parameters were used during the study. The typical parameters are summarized below. 2D multi-phase FSPGR was acquired with the Extended Dynamic Range (EDR) option, in-plane resolution of 0.63× 0.69 mm, 3.0 mm slice thickness and zero spacing, temporal resolution of 10.4 sec. per phase, TR/TE of 9.4/2.7 msec., RBW of 15.6 kHz and FA of 30°. 35 temporal phases were acquired at 5 imaging slice locations in 6:05 min. 3D T2w FSE was acquired using the EDR option with the in-plane resolution of 0.31×0.31 mm, slice thickness of 1.2 mm with 0.9 mm overlap, TR/TE of 900/27.4 msec., RBW of 15.6 kHz, using 4 signal averages leading to the total scan time of 7:57 min. (72 slices). 3D FIESTA was acquired using the EDR option with the in-plane resolution of 0.31×0.21 mm, slice thickness of 1.2 mm with 0.9 mm overlap, TR/TE of 14.7/4.2 msec., FA of 30°, RBW of 15.6 kHz, using 8 signal averages leading to the total scan time of 8:17 min. (72 slices). 3D IR-FSPGR was acquired with the in-plane resolution of 0.42× 0.38, slice thickness of 1.2 mm with 0.9 mm overlap, TR/TE/ TI of 15.9/7.6/200 msec., RBW of 15.6 kHz and FA of 25°, using 6 signal averages and total scan time of 8:32 min. (72 slices).

Acquired 3D data was rendered, reformatted and reviewed using Volume Viewer (Advantage Workstation, General Electric Healthcare). The location, size, shape and appearance of the ablation lesions were compared to those reported by the described post-processing method.

The dynamic contrast enhancement data was transferred to a stand-alone Linux computer equipped with four x86_64 Intel Xeon 3.0 GHz CPU's (HP xw8400, Hewlett Packard) and post-processed as described in above using software written in IDL v. 6.4 (ITT Visual Information Solutions) to execute the aforementioned method steps. The software simulated real-time working conditions by reading, post-processing and analyzing the dynamic series of MR images one by one, while recording the amount of time spent on each major step for each series.

Each dynamic series (all imaging slices acquired at a certain time instant) was read and post-processed by the software as a whole entity. A region of interest (ROI) was extracted from each slice (while the rest was not kept in the memory) and all the operations described below were performed on the ROIs. One of the slices was marked as the "main visualization" slice, whose lesion visibility was to govern the decision of continuing or interrupting data reading and processing. In some cases, the original images were low-pass filtered by a single passage of a 3×3 pixel averaging filter for the sake of comparison with the same non-filtered data. Equations 1, 4 and 13 were evaluated on several first pre-contrast agent dynamics on each slice. In some cases, the empty background pixels containing no tissue were suppressed for the sake of comparison with the same non-altered data.

Afterwards, CID, CIR and CES maps were calculated according to equations 14, and 5 correspondingly as well as the histogram of the current CES map was calculated and analyzed. A simple direct comparison algorithm compared the histogram bin values to identify two highest values and the lowest value located in-between the highest values.

The identified bin values and associated pixel intensity values were then compared to pre-defined thresholds (identified empirically) defining their separation in terms of both the number of pixels forming each bin and the pixel intensity values corresponding to those bins. As soon as the desired separation level was achieved for the "main visualization" slice, the software automatically stopped reading and post-processing temporal dynamic contrast enhancement dynamics, recorded the current dynamic contrast enhancement scan and software post-processing times, and switched to the lesion segmentation mode (thereby interrupting the image acquisition process).

Ablation lesions were then segmented from the latest (i.e. final) CES map. Segmentation was performed using either a segmentation threshold defined at the gray level having an intensity 5% higher than that of minimum bin value (identified in between the two maxima as described above), or by the Otsu method (25). Afterwards, the resulting lesion map's readability was enhanced by first erosion and then dilation by a single passage of 8-connectivity element (25) followed by low-pass filtering using a single passage of a 3×3 pixel averaging filter and output altogether with the corresponding CES, CID and CIR maps.

Also, three additional functions were calculated in parallel on the same data set (baselines and ROI's) for the sake of comparison—the traditional intensity difference (current intensity minus the baseline image one per pixel), traditional intensity ratio (current intensity divided by the baseline image one per pixel), and simple signal sum (intensity values at all available temporal dynamics summed per pixel). The time spent on calculating these comparative functions was not counted separately but was included in the total temporal dynamic post-processing time.

In a separate software run, the lesion-to-tissue contrast-to-noise ratio (CNR) and lesion profiles were calculated to compare the lesion border visualization capabilities of the present and traditional approaches. To calculate the CNR, two relatively small (~7-13×7-13 px) ROIs were chosen lying completely inside the lesion core and normally perfused tissue. The mean and standard deviation was calculated for both ROIs on the original dynamic contrast enhancement images as well as all maps derived from them. Then, the difference between the mean values calculated on the normal tissue and lesion core was divided by the sum of both standard deviations and the resulting lesion-to-tissue CNR was plotted as a function of time for each post-processing method. To calculate the lesion profiles, 3-5 rows or lines of pixels crossing ablation lesions were extracted from the original dynamic contrast enhancement images as well as all maps derived from them and averaged to form a single line or row. The resulting profiles were normalized to the dynamic range of [0;1] and plotted as a function of the spatial coordinate.

Figure 5A:
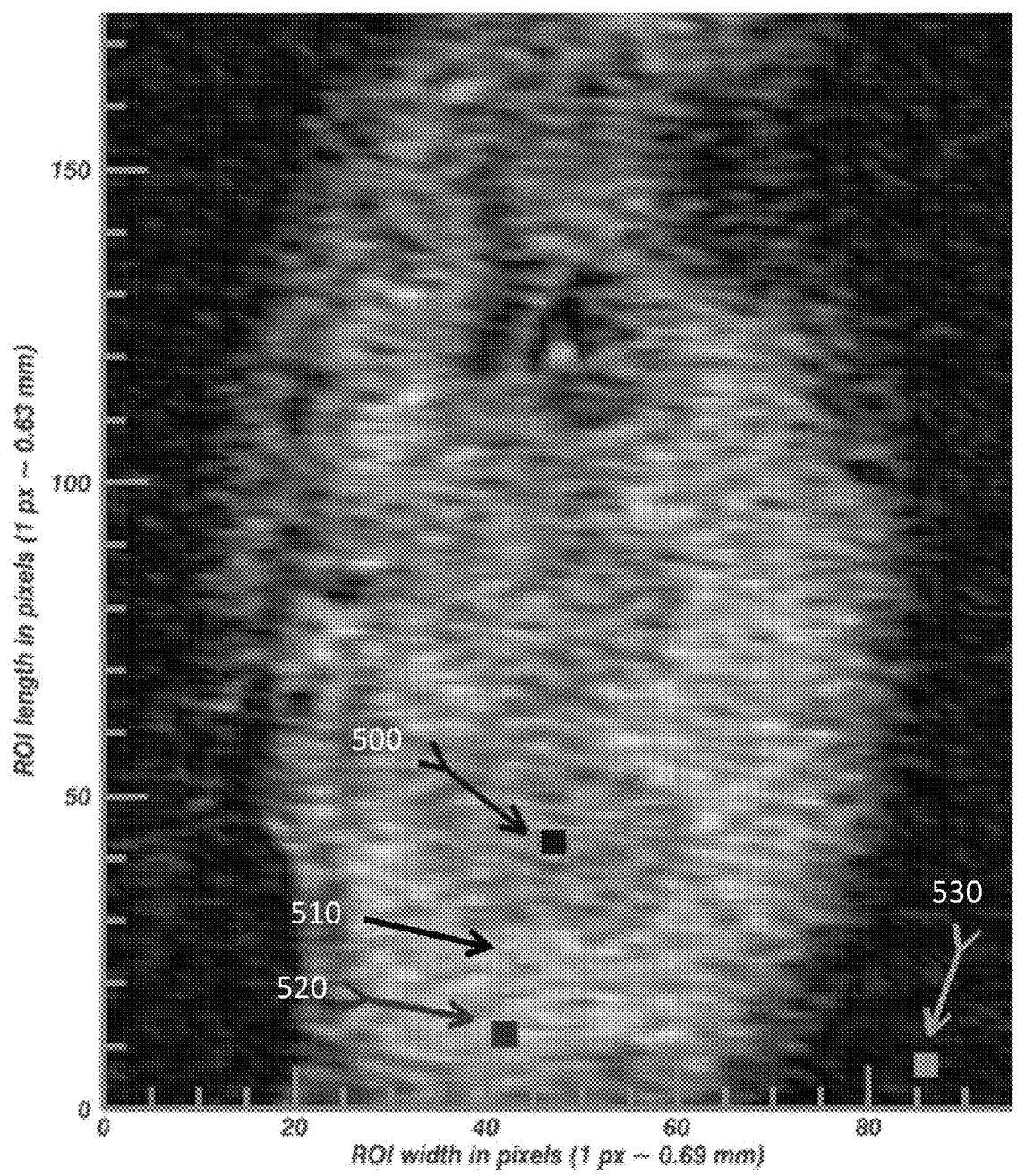
FIG. 5(a) shows a typical post-contrast agent injection DynCE image (as acquired) with squares marking single pixels whose time behavior was investigated. The squares are considerably bigger than 1 px and marked with arrows to enhance their visibility. The squares' and arrow's data curves time dependent pixel intensities are shown in FIG. 5(b). The ROI (region of interest) size is 65.3×109.3 mm (95×175 px).
Figure 5B:
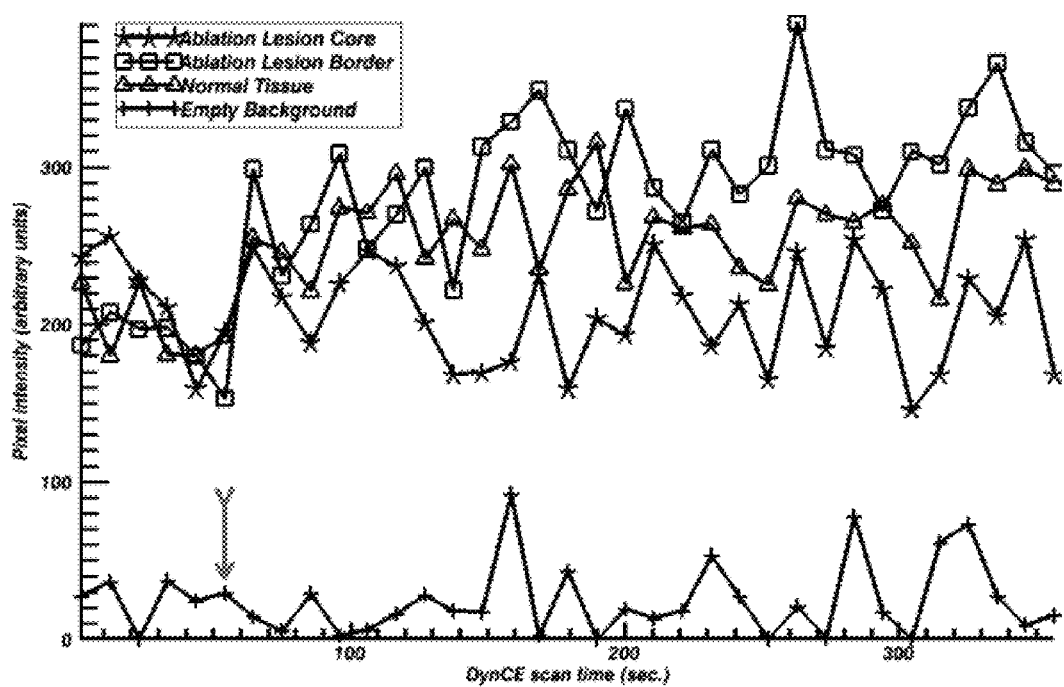
FIG. 5(b) shows intensity of the pixels marked on FIG. 5(a) plotted versus time through the whole scan. The vertical arrow marks the time at which contrast agent injection began. The data set was acquired ~2.5 hrs. after ablation.

FIG. 5($a$) depicts a typical for the reported study dynamic contrast enhancement image (after contrast agent injection), which has not undergone any post-processing. The small square ROIs mark locations around four single pixels, whose intensity was plotted versus dynamic contrast enhancement image acquisition time on FIG. 5($b$) as ablation lesion core 500, ablation lesion border 510, normal tissue 520, and empty background 530. The ablation lesion edge seems to experience a very weak CE as compared to the normal tissue and lesion core, however the differences are obscured by the image acquisition noise.

Figure 6A:
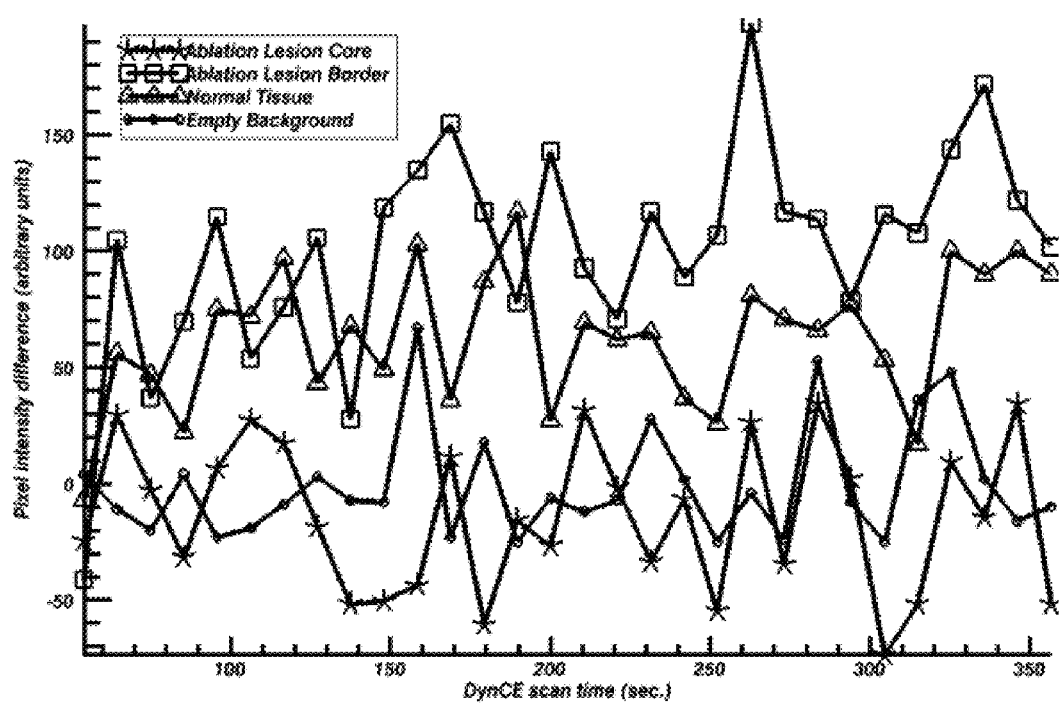
FIG. 6 plots (a) traditional intensity difference (b) traditional intensity ratio and (c) simple intensity sum calculated on the same ROI and data set for the same pixels depicted on FIG. 5. First five dynamic images (acquired before contrast agent injection started) were averaged to form the baseline used for calculating the difference and ratio. No noise reduction was applied on the original images.
Figure 6B:
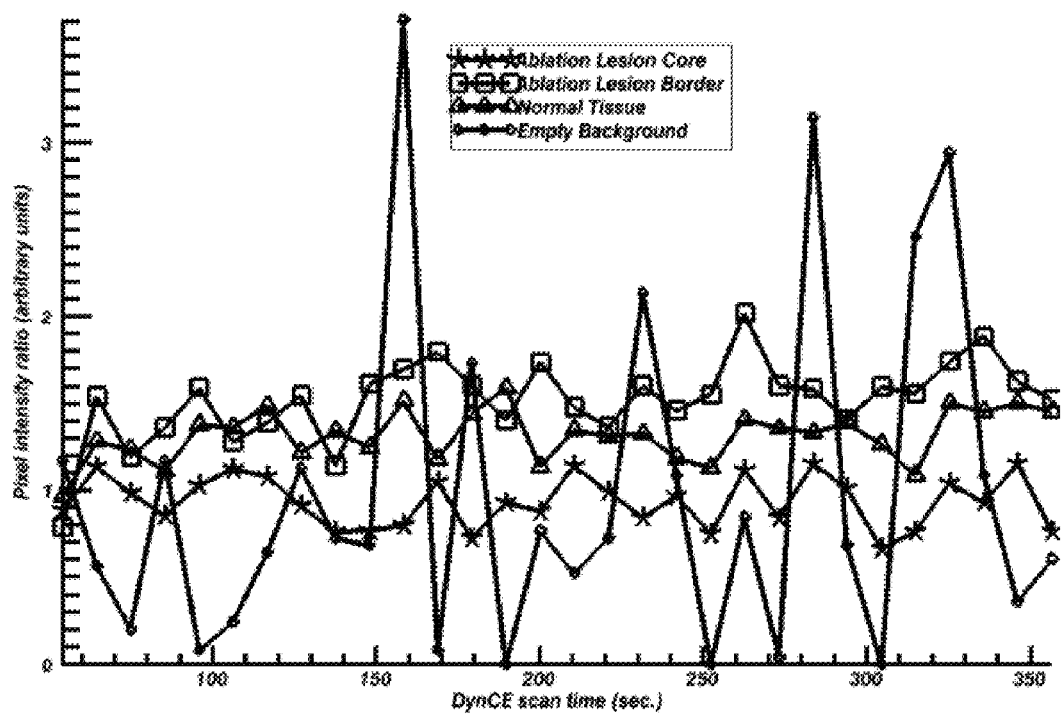
Figure 6C:
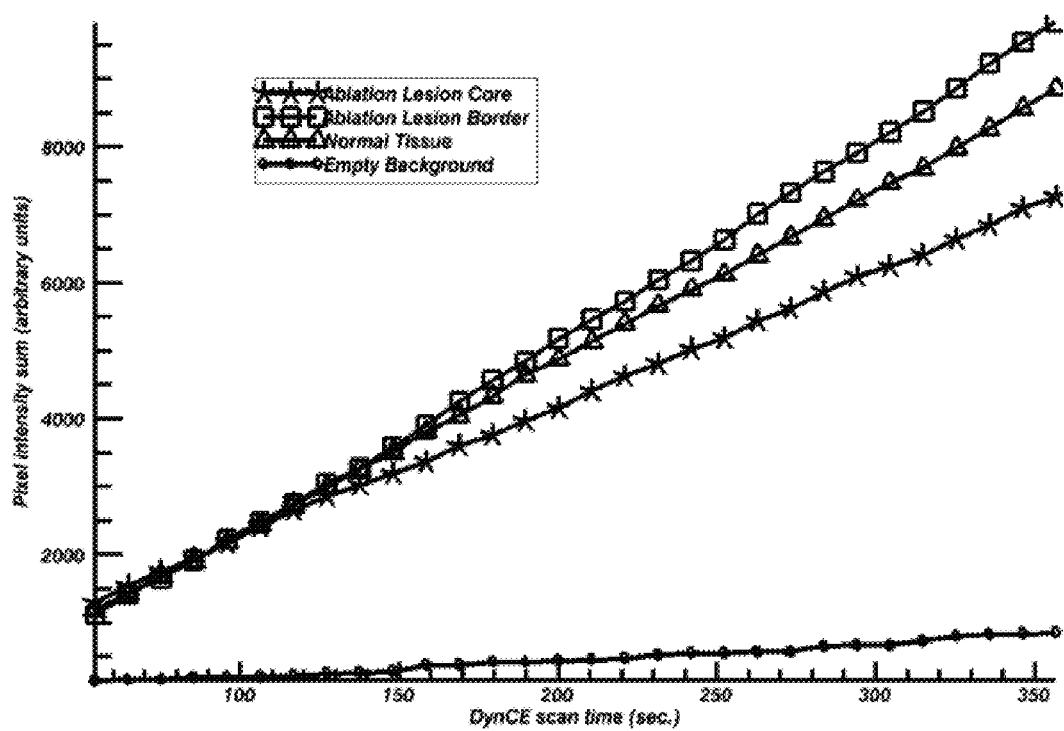

FIG. 6 depicts traditional difference and ratio as well simple signal sum (as functions of the dynamic contrast enhancement image acquisition time) calculated on the same data and under the same conditions as FIG. 5 (except for the five first dynamics averaged to form the baseline required for subtraction and division). The difference (FIG. 6($a$)) and ratio (FIG. 6($b$)) operations neither improve the contrast between pixels with different CE properties nor reduce the noise (as was expected). In contrary, the summation (FIG. 6($c$)) does lead to noise reduction due to the mutual cancellation of the noise-dominated terms (Appendix 3), which leads to improved discrimination between pixels with different CE properties in the very end of the scan.

Figure 7A:
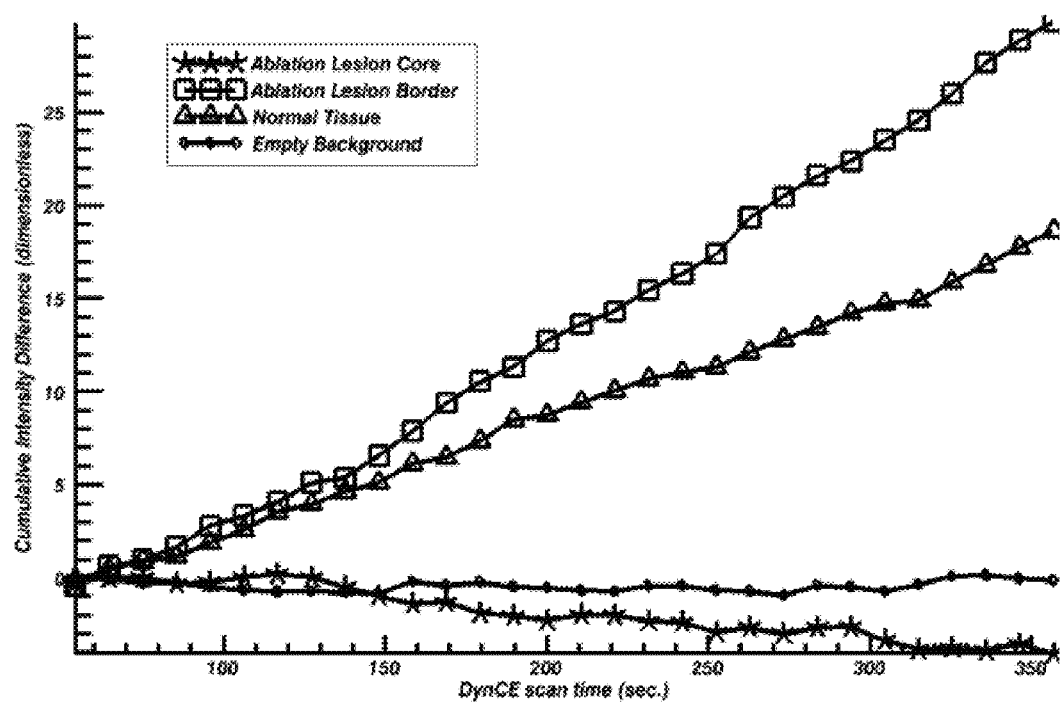
FIG. 7 plots (a) cumulative intensity difference (CID), (b) cumulative intensity ratio (CIR) and (c) cumulative enhancement sum (CES), calculated on the same ROI and data set for the same pixels depicted on FIGS. 5 and 6. The same baseline was used and no noise reduction was applied on the original images.
Figure 7B:
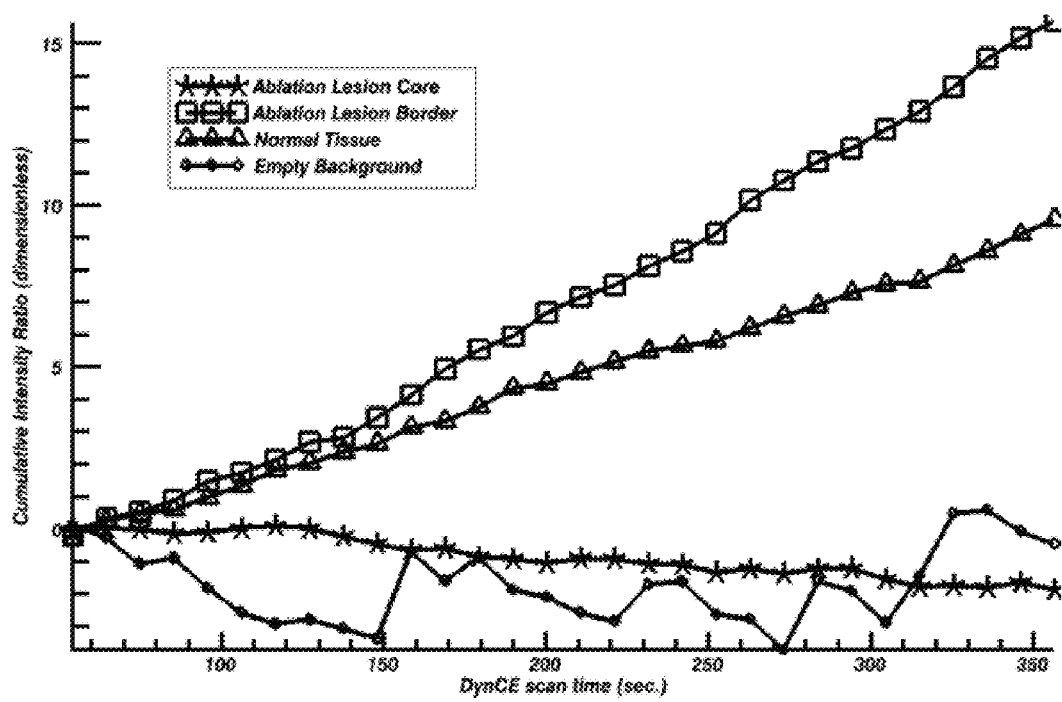
Figure 7C:
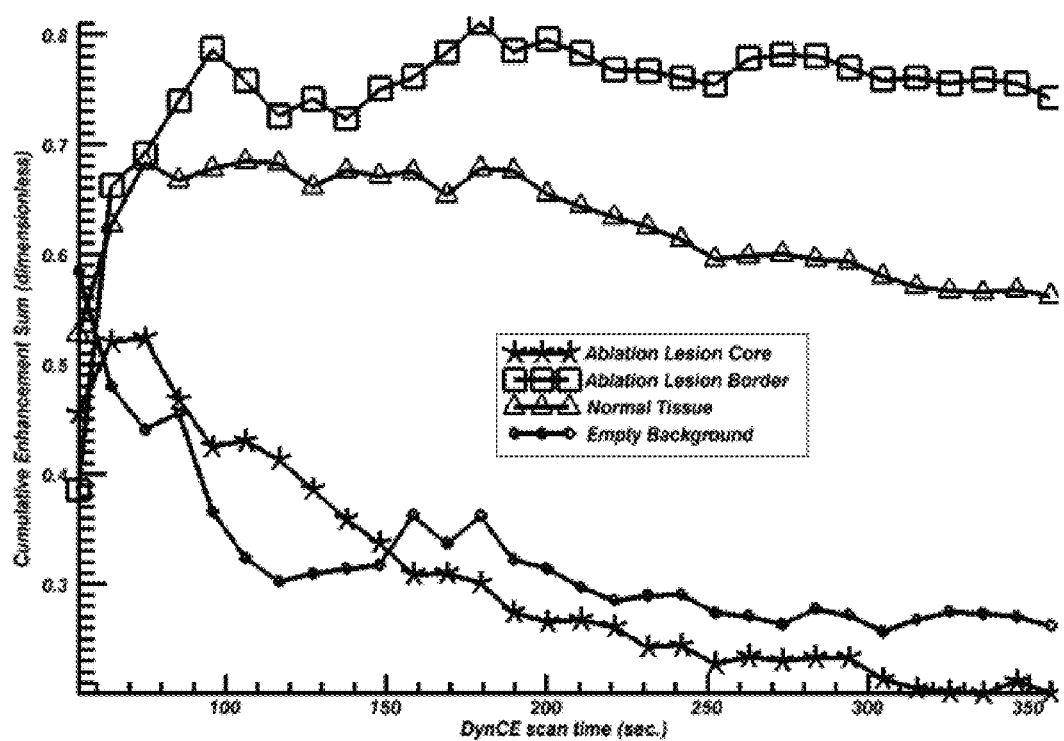

FIG. 7 depicts CID, CIR and CES curves (as functions of the dynamic contrast enhancement image acquisition time) for the same pixels as on FIG. 5 calculated on the same data and the same baseline as well as under the same conditions as the curves on FIG. 6, but according to equations 14, 15 and 5 correspondingly. Not only did the method substantially reduce the noise and improves discrimination between pixels with different CE properties, it also takes very few dynamic contrast enhancement dynamic images to achieve such discrimination. The CES value differences between the sample pixels (FIG. 7(c)) become apparent as early as ~45 sec. after contrast agent injection (~100 sec. dynamic scan time).

Figure 8:
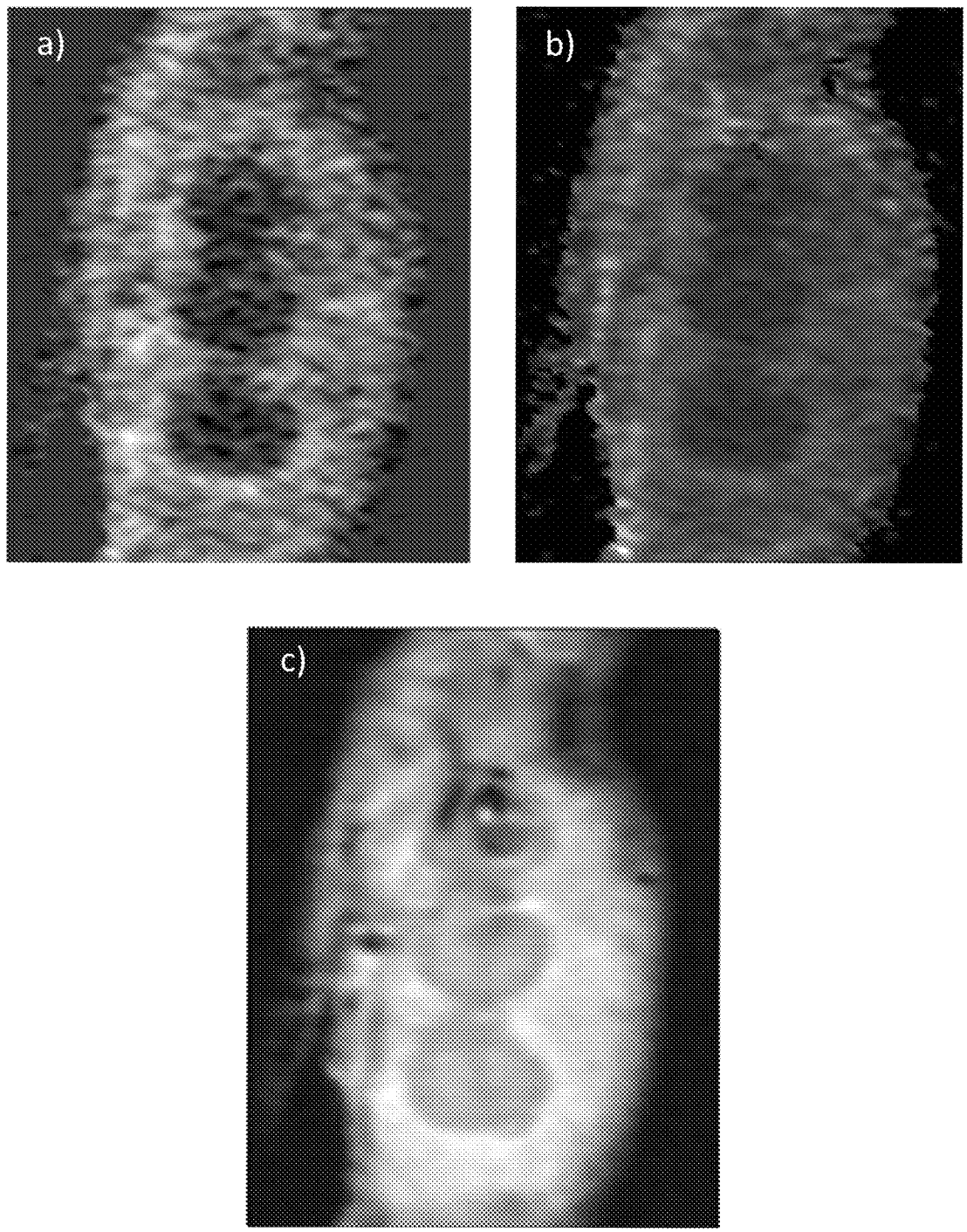
FIG. 8 shows images of (a) traditional intensity difference, (b) traditional intensity ratio, and (c) simple intensity sum calculated on the same ROI and data set depicted on FIGS. 5-7 from the last (in the temporal image acquisition series following contrast agent injection) dynamic images. First five dynamic images (acquired before contrast agent injection started) were averaged to form the baseline used for calculating the difference and ratio. The original images were low-pass filtered by a single passage of a 3×3 pixel averaging filter and empty background was suppressed by a histogram-based threshold.
Figure 9:
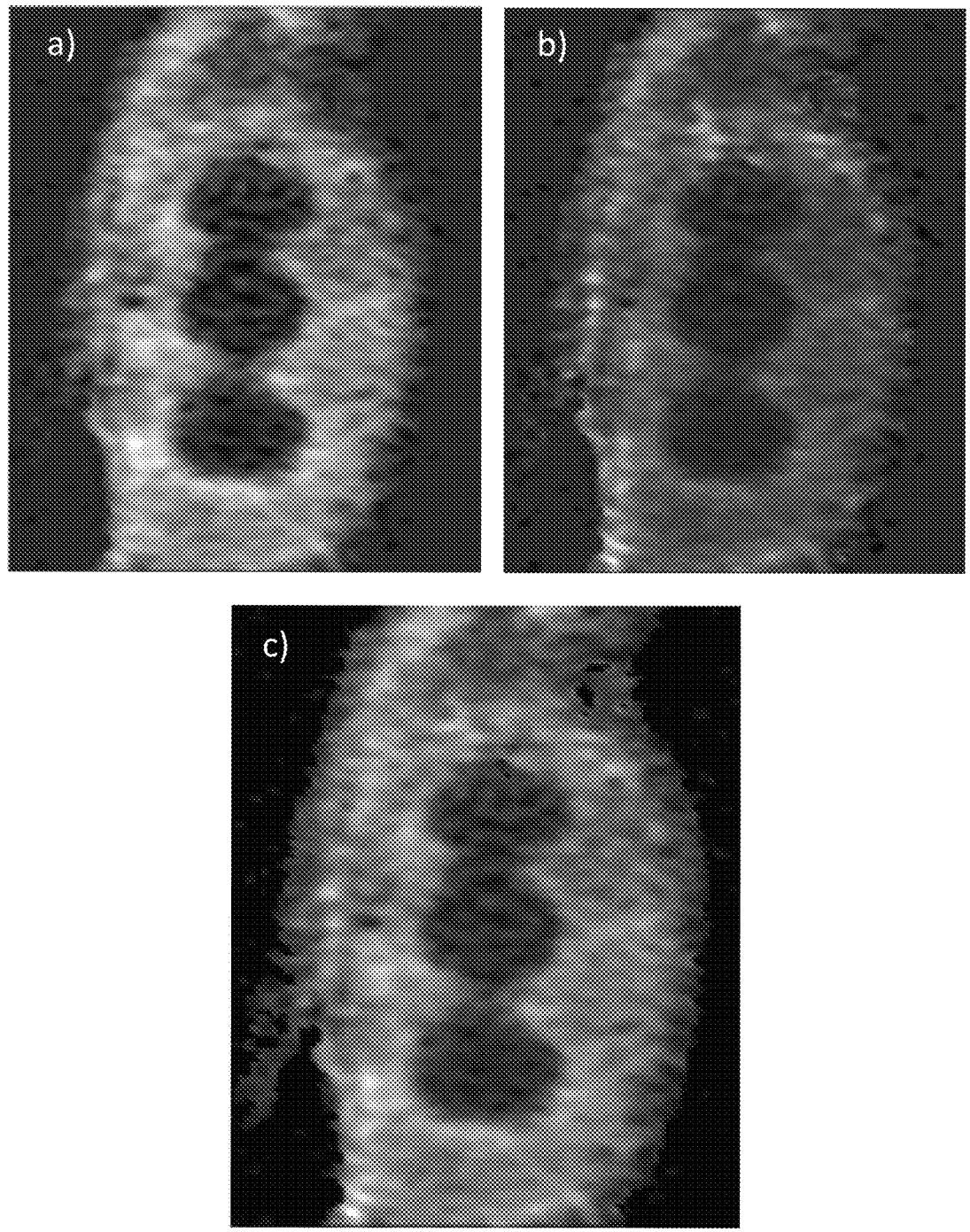
FIG. 9 plots the following cumulative maps: (a) CID, (b) CIR, and (c) CES calculated on the same ROI and data set as FIG. 8 from the last images. First five dynamic images (acquired before contrast agent injection started) were averaged to form the baseline used for calculating the difference and ratio. The original images were low-pass filtered by a single passage of a 3×3 pixel averaging filter and empty background was suppressed by a histogram-based threshold.
Figure 10:
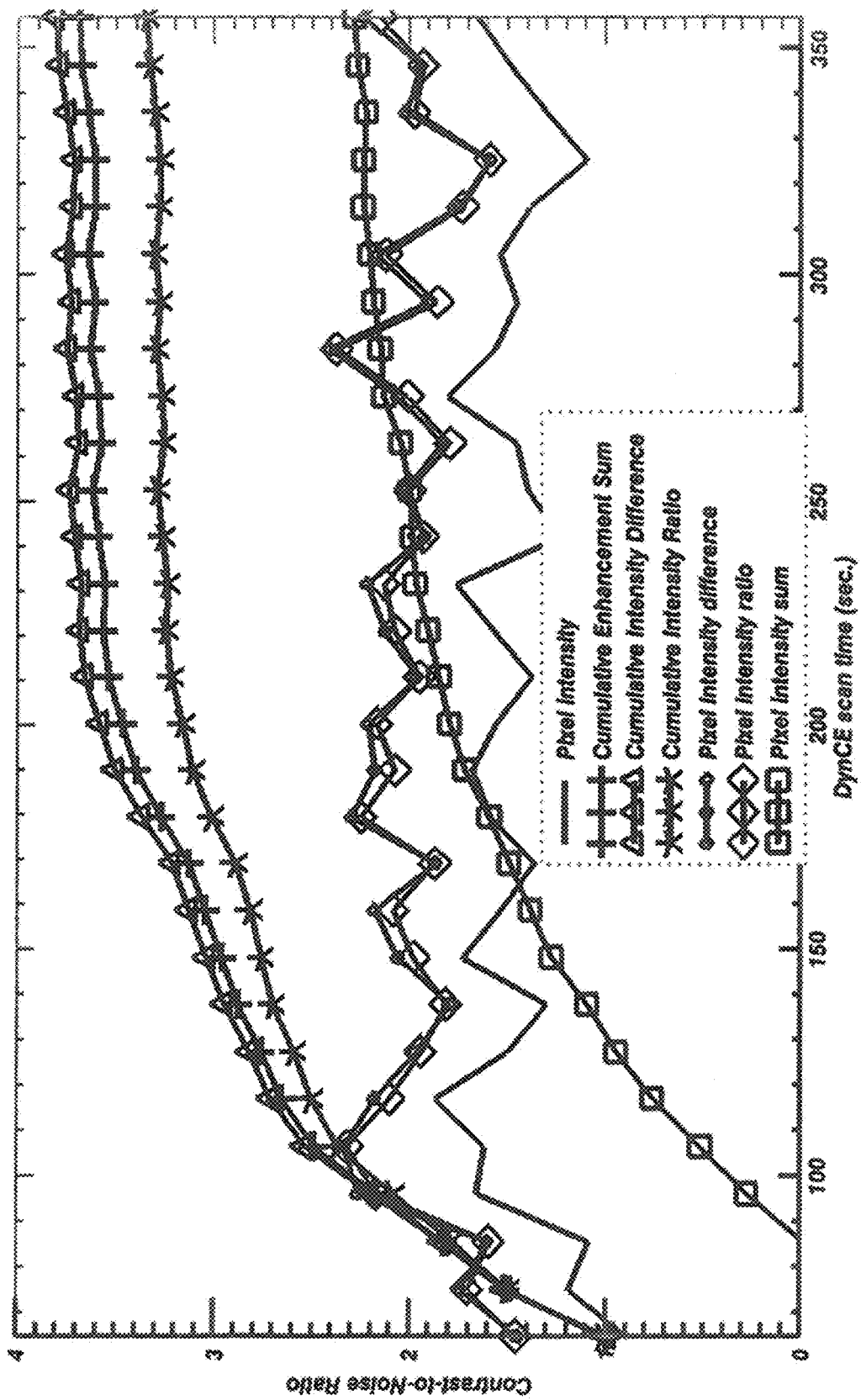
FIG. 10 shows comparative plots of lesion-to-tissue contrast-to-noise ratio (CNR) for the CID, CIR, CES, original images, as well as the traditional difference, ratio and simple sum. All the curves were calculated on the same data set (presented of FIGS. 8 and 9) and same baseline after the original images were low-pass filtered by a single passage of a 3×3 pixels averaging filter. Two 13×13 pixels ROI's were chosen inside the lesion core and normal tissue on the original images (FIG. 5(a)); difference, ratio and sum calculated for the sake of comparison (FIG. 8) and proposed cumulative characteristics (FIG. 9).
Figure 11A:
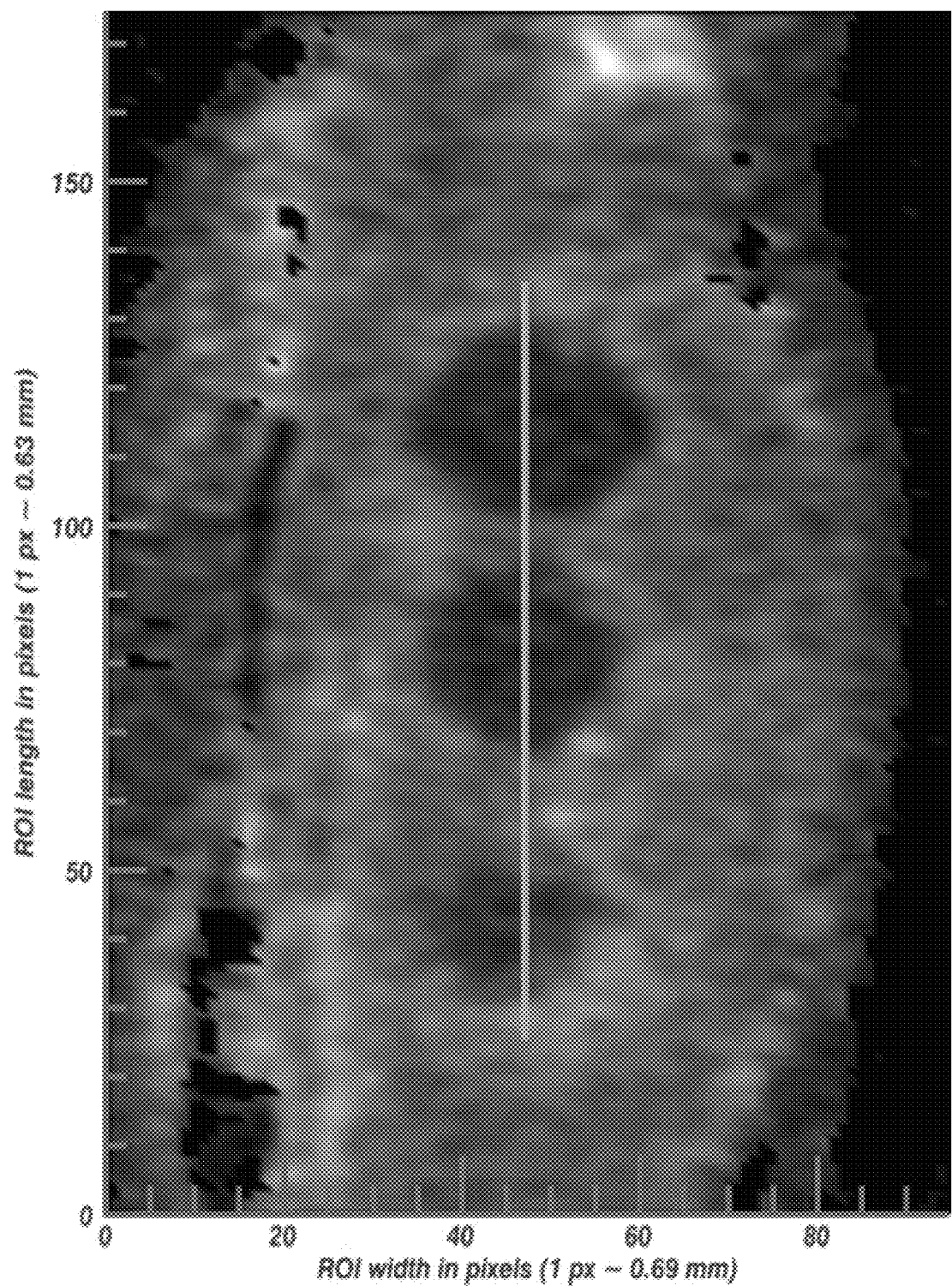
FIGS. 11 (a) and (c) plot a CES map depicting the sampling locations for the lesion profiles shown on FIGS. 11(b) and 11(d), respectively. For each sampling location, five adjacent columns or rows were extracted, averaged, normalized to the [0;1] range and plotted together for each compared characteristic.
Figure 11B:
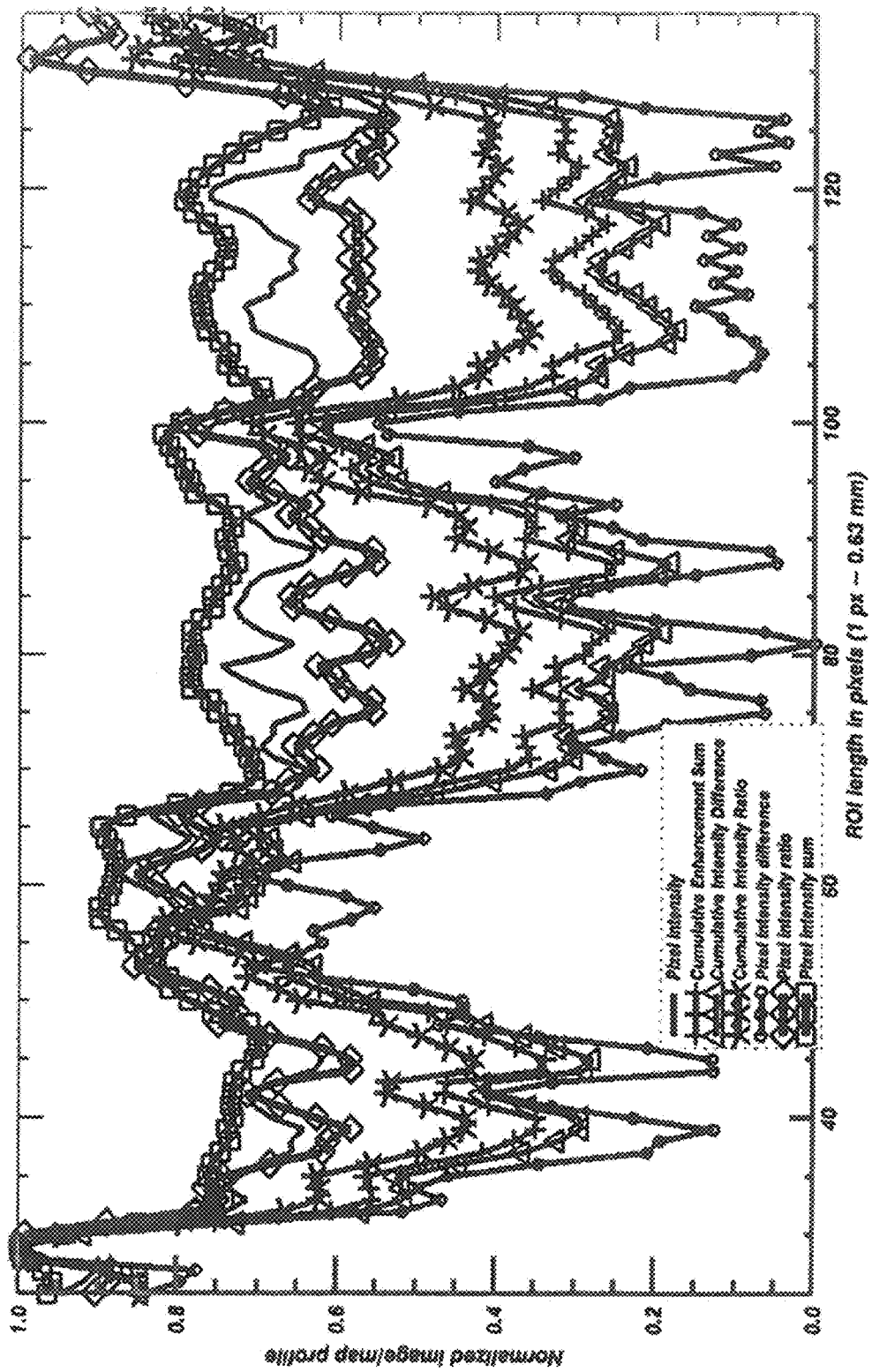
Figure 11C:
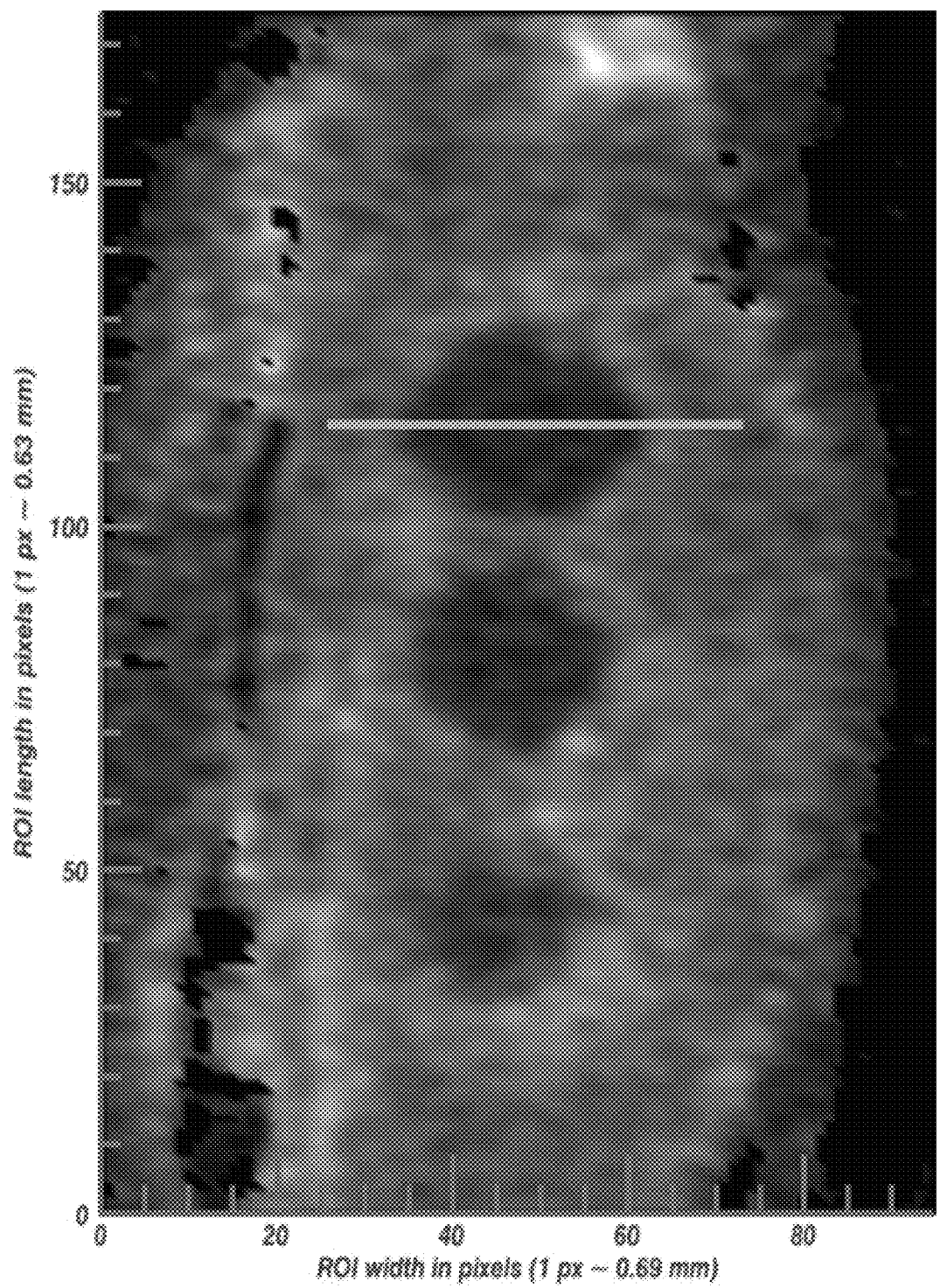
Figure 11D:
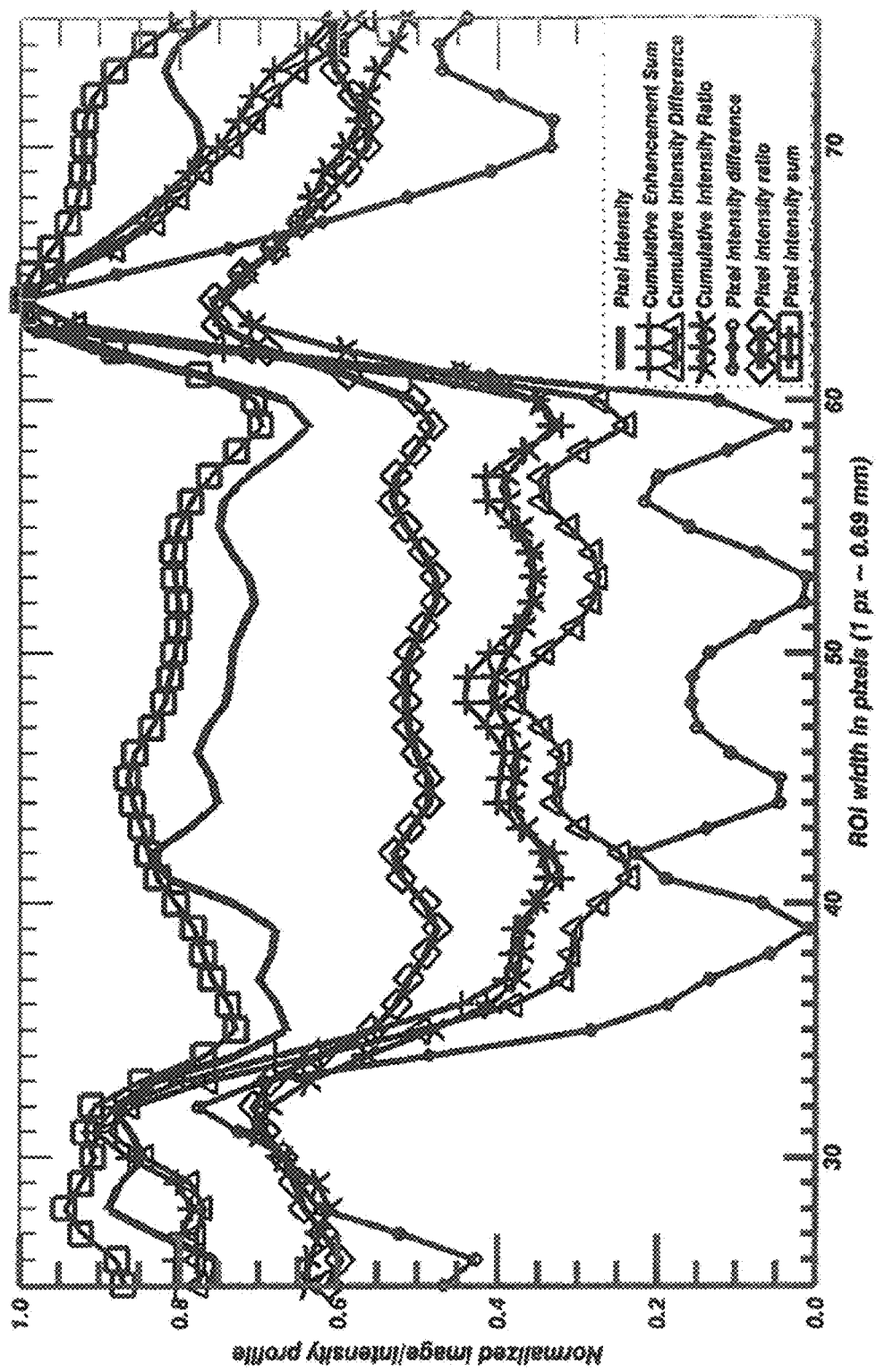

FIGS. 8 and 9 depict traditional difference, traditional ratio and simple intensity sum as well as CID, CIR and CES maps (correspondingly) calculated over the ROI depicted on FIG. 5(a) in the end of the dynamic contrast enhancement acquisition. The present method provides superior ablation lesion visualization in the terms of better lesion-to-tissue contrast and more accurate lesion border delineation. This improvement is quantified on FIG. 10, which depicts the time behaviour of the lesion-to-tissue CNR during the whole dynamic contrast enhancement scan. The present cumulative approach is thus twice more sensitive to the differences in the CE properties between ablation lesions and normal tissue in spite of the noise obscuring them, which implies better lesion border delineation. FIG. 11 confirms this conclusion. CES, CID and CIR exhibit the most homogenous lesion core and gap profiles as well as the most sharp lesion borders. The traditional difference produces even deeper lesion core profiles, but is very vulnerable to the noise, so both lesion core and gap profiles are distorted by noise spikes so much, that identification of the real lesion borders becomes challenging.

Figure 12A:
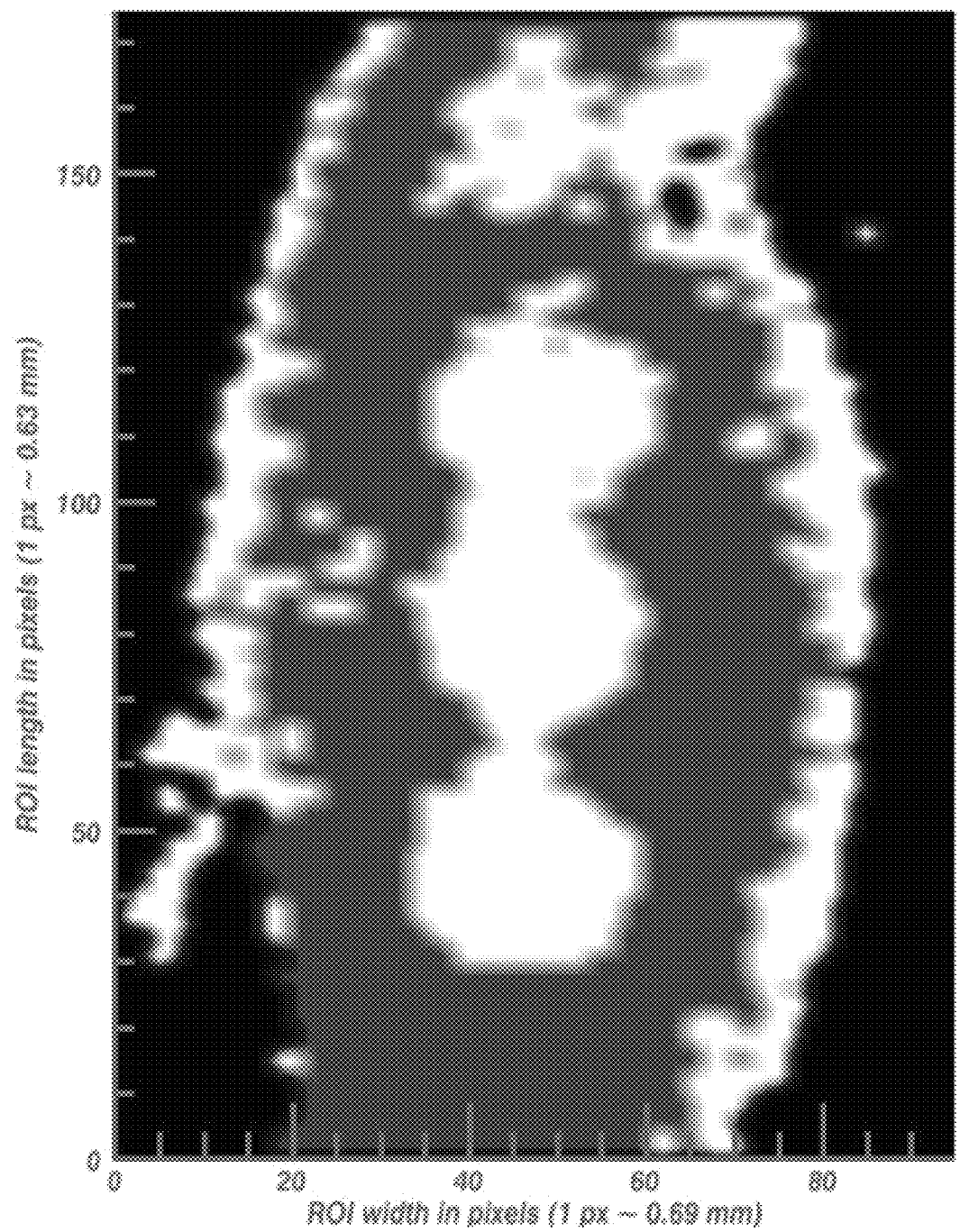
FIG. 12(a) shows lesion maps segmented by the Otsu method from the CES obtained during the experiment illustrated on FIG. 5 at the DynCE scan time 159 sec., which is 104 sec. after contrast agent injection and 206 sec. before the scan end. The non-perfused pixels are marked in white, perfused—in gray, and empty background ones—in black.
Figure 12B:
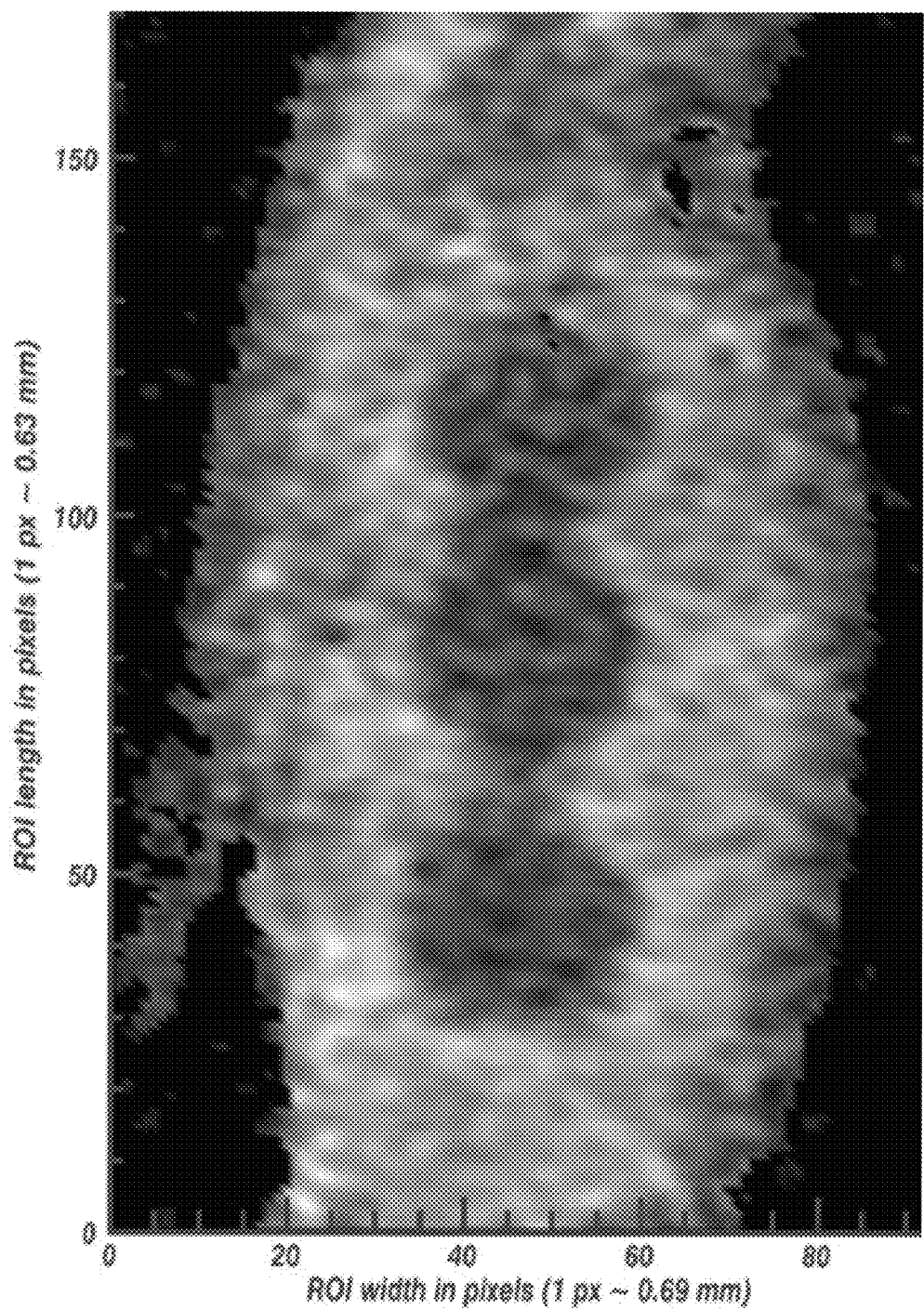
FIG. 12(b) shows a CES map from which the lesion map was segmented.
Figure 12C:
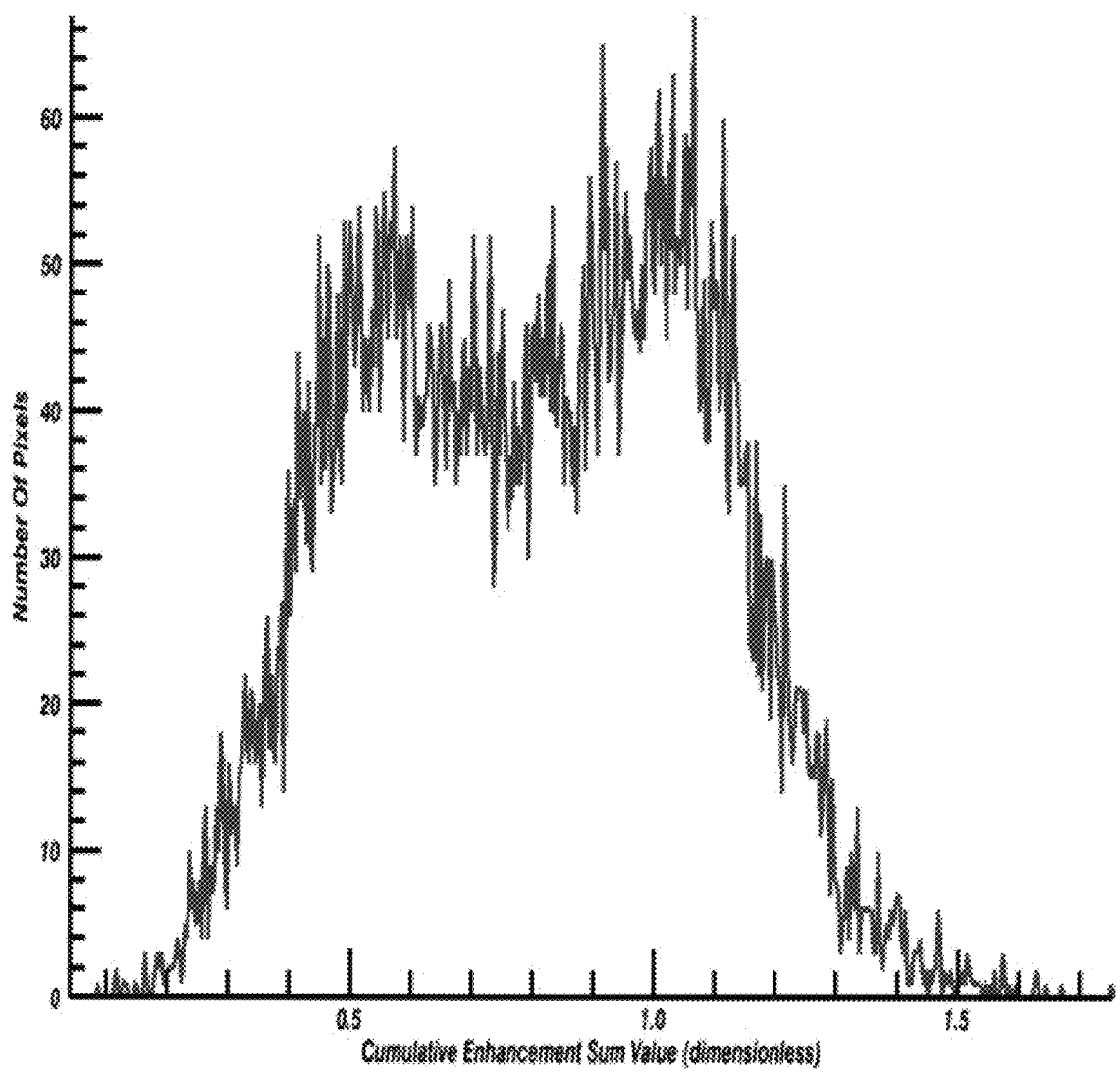
FIG. 12(c) plots the CES map's histogram (no smoothing was applied; the empty background peak around the zero value is not shown).
Figure 13:
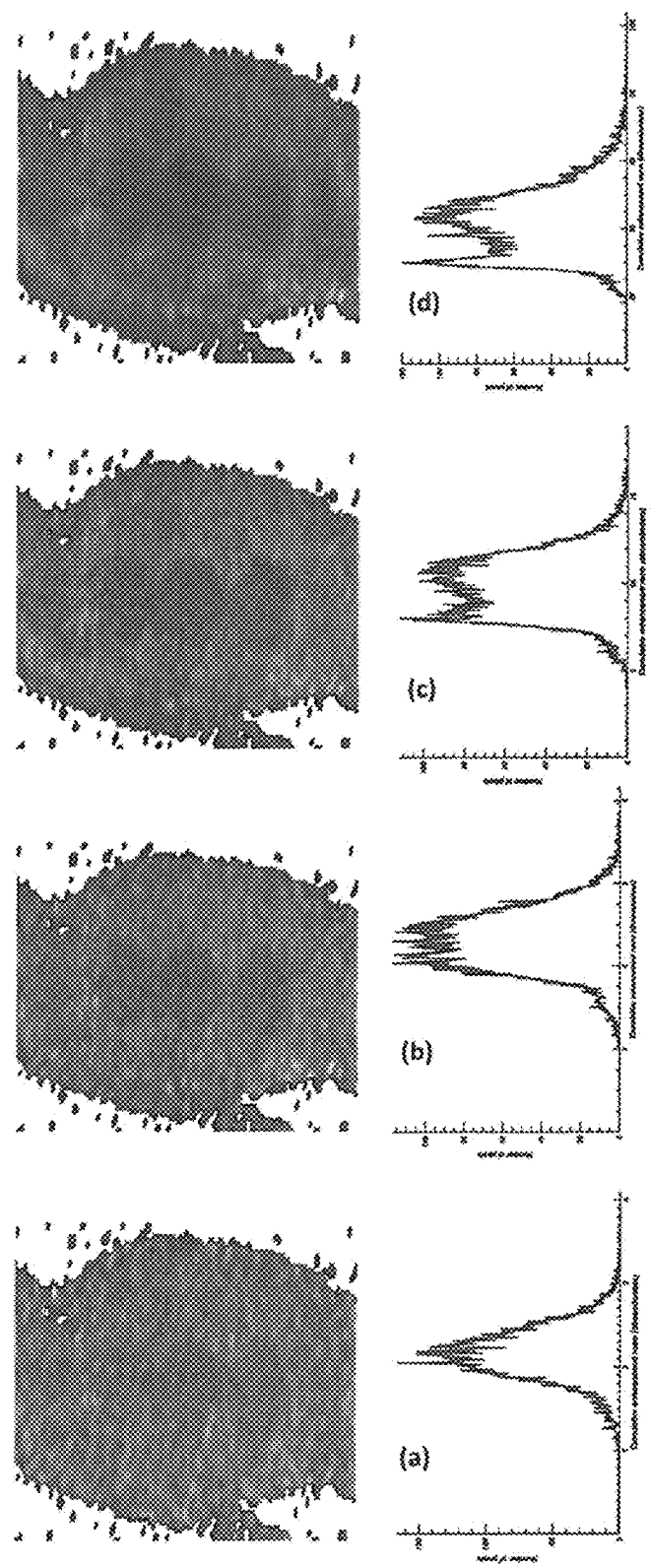
FIGS. 13(a)-(d) illustrate the time-dependent shape change in the development of the histogram, along with the corresponding CES maps.

FIG. 12(a) depicts the lesion map segmented from the dynamic contrast enhancement data represented by FIG. 1 from the CES calculated at 159 sec. from the scan beginning (FIG. 12(b)), which is 104 sec. after contrast agent injection and 206 sec. before the ending of the actual data acquisition procedure. At this moment, the automatic histogram analysis algorithm found that the typical maxima at the CES map's histogram are separated enough to provide sufficient lesion visualization and stopped the processes of reading and post-processing the dynamic contrast enhancement data. FIGS. 13(a)-(d) illustrate the time-dependent shape change in the histogram, along with the corresponding CES maps. The segmented lesion map depicts correctly the three ablation lesions in the center, the non-perfused rim at the edge of the animal's body (occupied by physiological solution, which was powered onto the muscle to enable electrical conduction during the ablation and stayed trapped under the skin) as well as the fold between the animal's thigh and trunk, which was filled with air and did not generate enough MRI signal due to the partial volume effect (the non-perfused area above the uppermost lesion).

The post-processing time was ~0.64 sec. per dynamic, which included: reading 5 images (by the number of imaging slices acquired at each dynamic) from the hard drive, segmenting 95×175 pixels ROI's from each image (83125 pixels altogether), smoothing them with a single passage of the 3×3 pixels averaging filter, identifying the empty background pixels, calculating CID, CIR and CES maps as described above section for each ROI, calculating the traditional intensity difference, traditional intensity ratio, and simple signal sum as described above for the sake of comparison, calculating the CES map's histograms for each slice, smoothing them with 2-3 passages of a 7 pixels wide averaging pixels, identifying two global maxima, testing the maxima and the minimum between them according to the pre-defined relative height and separation criteria, taking the "stop or read again" decision. The few first pre-contrast agent dynamics were post-processed in considerably less time—~0.47 sec., while the five baseline images, normalization constants and correction terms (equations 1, 4 and 13 correspondingly) were calculated in ~0.27 sec. These results are typical.

In all of the present experiments, the post-processing time per dynamic was less than 1 sec., which was always considerably less than the acquisition time for a single dynamic. After the "stop" decision was generated, it took ~1.2 sec. to segment (by the Otsu method) and to smooth (by first erosion and then dilation using a single passage of 8-connectivity element followed by single passage of a 3×3 pixel averaging filter) all five lesion maps. In total, the whole post-processing time for the data set was ~10 sec. beginning at the moment the first image was read from the hard drive and ending the moment the final lesion map for the visualization slice was output (FIG. 12(a)).

Figure 14A:
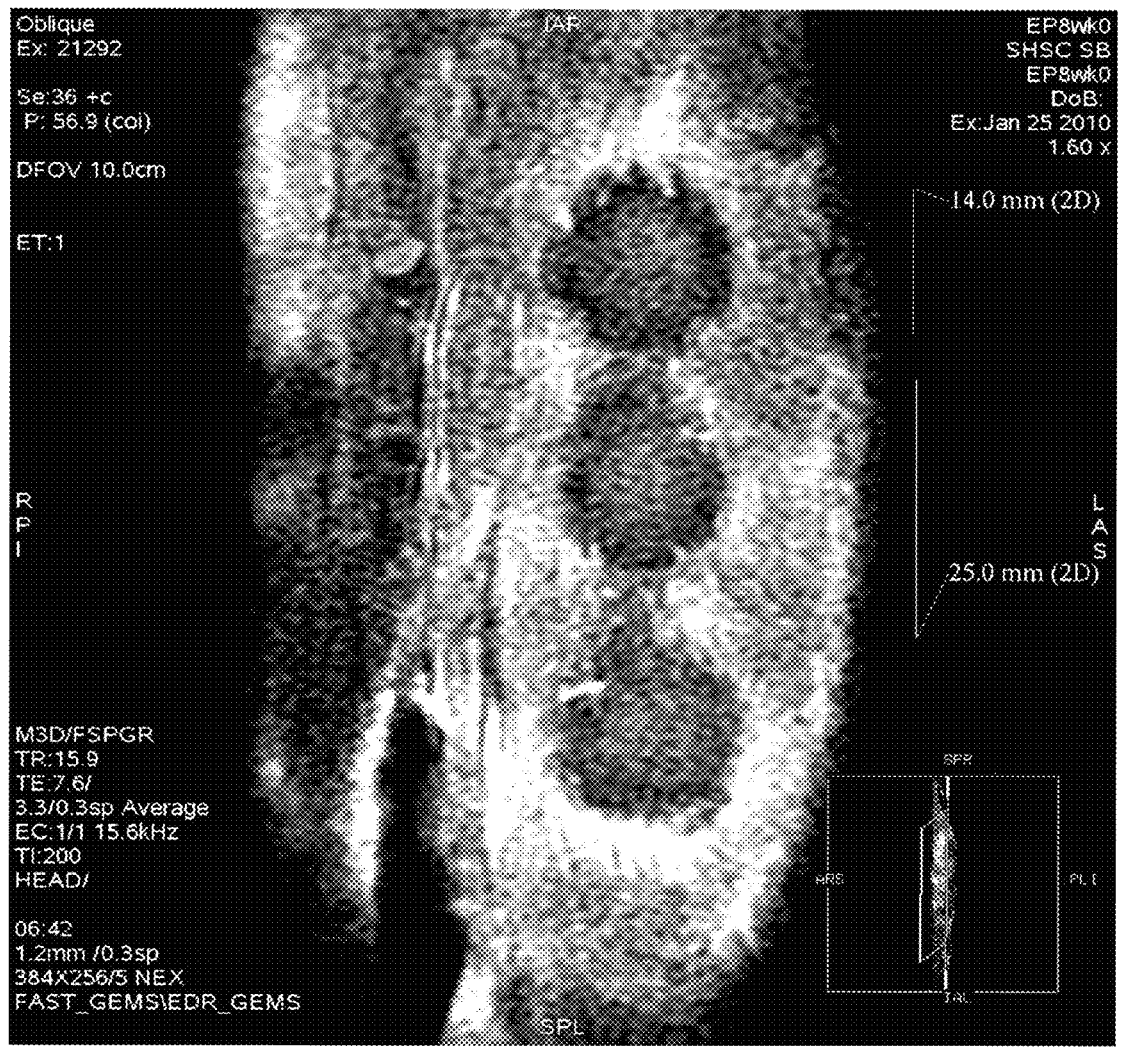
FIGS. 14 (a) and (b) show post-CA IR FSPGR (also referred to as delayed enhancement) images reformatted to coincide spatially with the DynCE slices shown on FIGS. 9 and 11, respectively.
Figure 14B:
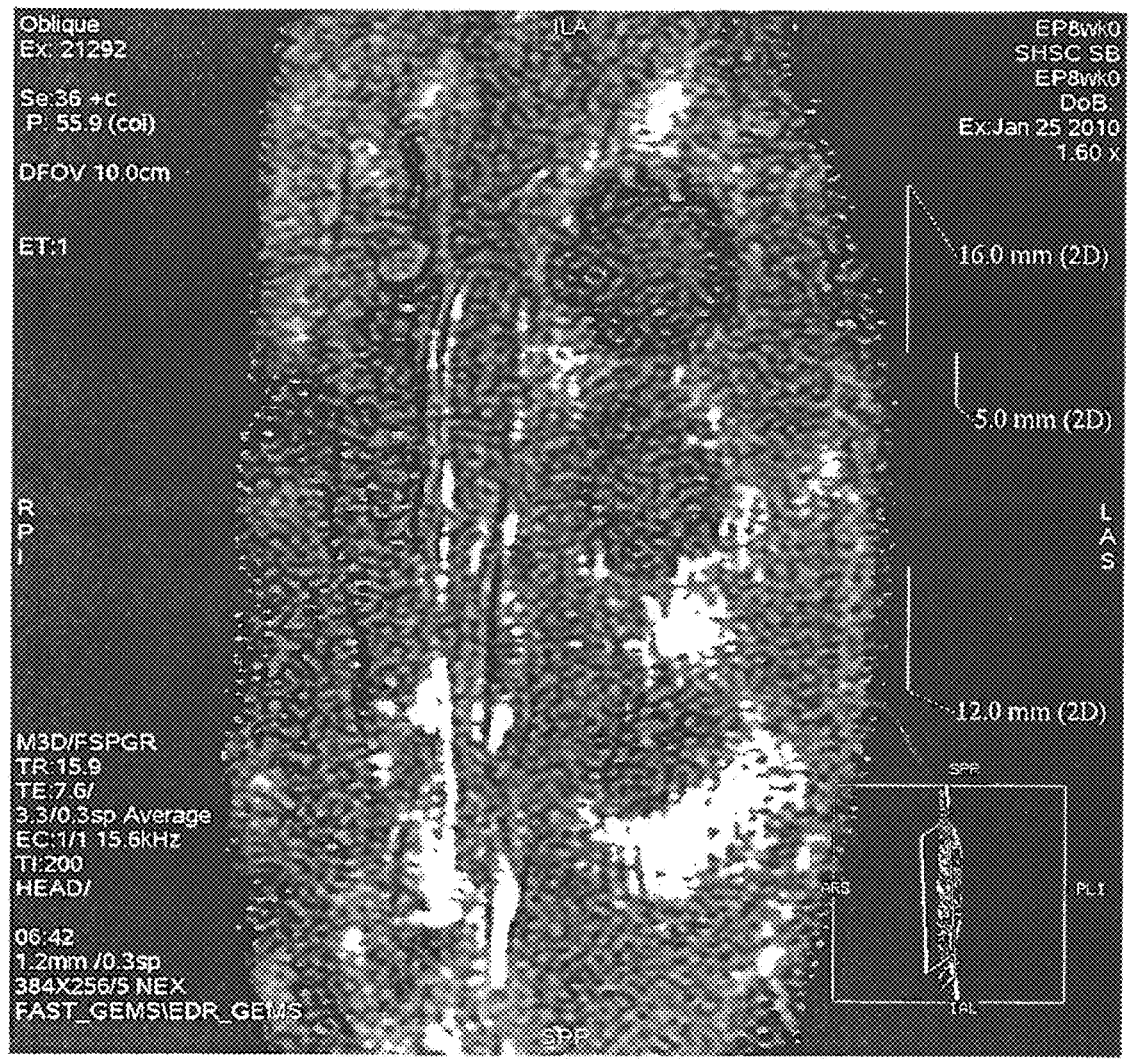

FIG. 14 shows 3D IR-FSPGR data set reformatted to coincide with the locations of the dynamic contrast enhancement slices depicted on FIGS. 9 and 11. In all the experiments, the cumulative and lesion maps coincided very well with the lesion representations depiction by the conventional methods (T2w, SSFP and DE imaging).

In general, the proposed cumulative characteristics enabled good ablation lesion visualization and segmentation without any user interaction on the cost of rather small post-processing times rather shortly (usually, 1-1.5 min.) after contrast agent injection, well before the end of the dynamic contrast enhancement dynamic series.

The described method has demonstrated good performance on all lesions regardless of their age. The one week old lesions had the most bright and sharp hyper-enhancement rim, which improved lesion border visibility. However, the method's performance on fresh (~2-3 hrs. old) lesions was good, which suggests its applicability during EP ablation cases.

CID, CIR and CES maps seem to be rather similar, so one would consider that any one may be sufficient. However, as FIG. 7(c) suggests, the CES map develops the proper lesion-to-tissue contrast the earliest. It enables fast lesion visualization at 100 sec. of dynamic contrast enhancement scan time (45 sec. after contrast injection), while the rest of the methods are still does not provide sufficient differentiation between pixels with different CE properties. However, it does contain the noise from both CID and CIR, so its CNR behaves close to CID (by FIG. 10). As suggested by FIG. 11, CES offers the best compromise between the flatness and sharpness of the lesion profile. This may be the reason why in many experiments CES maps provide apparent better lesion edge delineation for the naked investigator's eye.

APPENDICES

Appendix 1

A pixel's magnitude image intensity can be represented as (21)

$$M = \sqrt{(S_R + \eta_R)^2 + (S_I + \eta_I)^2} \quad [A1\text{-}1],$$

where $S_R$ and $S_I$ are real and imaginary parts of the acquired signal, while $\eta_R$ and $\eta_I$ are zero-mean normally distributed random variables describing the measurement noise in the real and imaginary channels correspondingly. Eq. [A1-1] can be re-written as $$M = \sqrt{\frac{(S_R + \eta_R)^2 + (S_I + \eta_I)^2 + 2(S_R + \eta_R)}{(S_I + \eta_I) - 2(S_R + \eta_R)(S_I + \eta_I)}} = \quad [A1\text{-}2]$$

$$= \sqrt{[(S_R + \eta_R) + (S_I + \eta_I)]^2 - 2(S_R + \eta_R)(S_I + \eta_I)} =$$

$$= \sqrt{[(S_R + \eta_R) + (S_I + \eta_I)]^2 \times \left(1 - \frac{2(S_R + \eta_R)(S_I + \eta_I)}{[(S_R + \eta_R) + (S_I + \eta_I)]^2}\right)}$$

Taking into the account the fact that the second term in Eq. [A1-2] (the one in parenthesis) is always real and positive (as well as less than unity since the denominator of the fraction is always greater than the fraction's nominator) and all the involved parameters are real, Eq. [A1-2] can be re-written as $$M = |(S_R + R_I) + (\eta_R + \eta_I)| \times \sqrt{1 - \frac{2(S_R + \eta_R)(S_I + \eta_I)}{[(S_R + \eta_R) + (S_I + \eta_I)]^2}} = \quad [A1\text{-}3]$$

$$\text{sign}(S_R + S_I + \eta_R + \eta_I) \times [(S_R + S_I) + (\eta_R + \eta_I)] \times$$

$$\sqrt{1 - \frac{2(S_R + \eta_R)(S_I + \eta_I)}{[(S_R + \eta_R) + (S_I + \eta_I)]^2}} =$$

$$(S_R + S_I) \times \text{sign}(S_R + S_I + \eta_R + \eta_I) \times$$

$$\sqrt{1 - \frac{2(S_R + \eta_R)(S_I + \eta_I)}{[(S_R + \eta_R) + (S_I + \eta_I)]^2}} + +(\eta_R + \eta_I) \times$$

$$\text{sign}(S_R + S_I + \eta_R + \eta_I) \times \sqrt{1 - \frac{2(S_R + \eta_R)(S_I + \eta_I)}{[(S_R + \eta_R) + (S_I + \eta_I)]^2}},$$

Both terms summed in Eq. [A1-3] are dependent on both signal and noise values in the acquisition channels. They are added equally with the same weighting coefficient (which is also dependent on both signal and noise values in the acquisition channels) to form the magnitude image. However, the first term is proportional to $(S_R+S_I)$, so its contribution to the final sum is mainly dominated by the acquired signal values. As for the second one, it is proportional to $(\eta_R+\eta_I)$, so its contribution to the final sum is mainly dominated by the acquisition noise and its behaviour approximates that one of the acquisition noise. Thus, one can consider the magnitude image intensity as being a sum of two different components—"mainly signal" and "mainly noise" ones. A post-processing method, which could reduce the contribution of the second component only, would be able to improve the visibility of the useful image features conveyed by the first component.

$S_R$ and $S_I$ depend on the properties of the imaged object and scan conditions, so they do not vary unless those properties and/or conditions change. Both $\eta_R$ and $\eta_I$ are normally distributed around the zero mean, so they can be either positive or negative with equal probability. Thus, for high SNR cases (i.e., $S_R+S_I>\eta_R+\eta_I$), the noise-dominated term will cause the magnitude image intensity M to be either larger or smaller than the $(S_R+S_I)$-dominated value by depending on whether $(\eta_R+\eta_I)$ is positive or negative correspondingly. If sampled during a time period, the measured values of M will be distributed on the both sides around the signal-dominated term, which provides a biased (by a coefficient, which is less than unity) estimate of the true acquisition signal. For low SNR cases (i.e., $S_R+S_I<\eta_R+\eta_I$), the $(\eta_R+\eta_I)$-dominated terms will become strictly positive since they will define $\text{sign}(S_R+S_I+\eta_R+\eta_I)$. So, sampling during a period of time will deliver a distribution around a positive constant dependent on the statistical properties of the measurement noise ($\eta_R$ and $\eta_I$) per se. Both conclusions are in a very good concordance with the previously reported analyses (e.g.: FIG. 1 of 21, FIG. 4 of 20, etc.).

Thus, the magnitude image pixel intensity can be considered as being a sum of two terms—signal-dominated and noise-dominated ones, and the noise-dominated term can be either positive or negative for pixels producing higher signal values as well as distributed around a positive constant for low-signal pixels (e.g. empty spaces on the FOV).

Appendix 2

The present example assumes, for purposes of illustration, that a dynamic series of magnitude images is acquired using a T1w RF-spoiled Gradient Echo sequence with a fixed set of imaging parameters while contrast agent is washed into and/or from the imaged anatomy. In this case, the image voxel intensity is a function of the contrast agent concentration only and can be represented as (24):

$$M(C) = \rho_0 \times \sin(\theta) \times \frac{1 - E_1(C)}{1 - \cos(\theta) \times E_1(C)} \times E_2(C) \quad [A2\text{-}1]$$

$$E_1(C) = \exp\left[-TR \times \left(\frac{1}{T1} + \alpha_1 C\right)\right] \quad [A2\text{-}2]$$

$$E_2(C) = \exp\left[-TE \times \left(\frac{1}{T2^*} + \alpha_2 C\right)\right], \quad [A2\text{-}3]$$

as well as C is the contrast agent's concentration; $\rho_0$ is the voxels spin density; $\theta$, TE and TR are the flip angle, echo time and repetition time of the pulse sequence; T1 and T2* are the inherent relaxation times of the tissue occupying the voxel (in the absence of any contrast agent); $\alpha_1$ and $\alpha_2$ are the longitudinal and transverse relaxivities of the contrast agent correspondingly.

Since the denominator in Eq. [A2-1] cannot approach zero under the practical imaging conditions and both $E_1(C)$ and $E_2(C)$ are n times differentiable by C, i.e.

$$\frac{d^n E_1}{dC^n} = (-1)^n (\alpha_1 TR)^n E_1, \quad [A2\text{-}4]$$

$$\frac{d^n E_2}{dC^n} = (-1)^n (\alpha_2 TE)^n E_2, \quad [A2\text{-}5]$$

then M(C) can be evaluated using Taylor's expansion for any $\Delta C \in [0; C_{max}]$ as $$M(\Delta C) = M(0) + \sum_{k=1}^{n-1} \frac{1}{k!} M^k(0) \Delta C^k + R_n(\Delta C), \quad [A2\text{-}6]$$

where $C_{max}$ is the maximum contrast agent concentration achieved during the experiment and $R_n(\Delta C)$ is a residual. In particular, for small $\Delta C$ values, when the non-linear on $\Delta C$ terms can be omitted, $$M(\Delta C) \approx M(0) + \quad [A2\text{-}7]$$

$$\left[\alpha_1 TR \frac{E_1(0) E_2(0)(1 - \cos\theta)}{(1 - E_1(0)\cos\theta)^2} - \alpha_2 TE \frac{E_2(0)(1 - E_1(0))}{(1 - E_1(0)\cos\theta)}\right] \Delta C.$$

As it follows from Eqs. [A2-6] and [A2-7], the magnitude image pixel intensity on a CE T1-weighted image can be represented as a sum of two terms, where the first term contains the signal arising due to the inherent MRI properties of the tissue occupying the imaged voxel (if any), and the second term contains the signal increment due to the infusion of the contrast agent into the imaged voxel (if any).

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

REFERENCES

1. Dickfeld T, Kato R, Zviman M, Nazarian S, Dong J, Ashikaga H, Lardo A C, Berger R D, Calkins H, Halperin H. Characterization of acute and subacute radiofrequency ablation lesions with nonenhanced magnetic resonance imaging. Heart Rhythm 2007; 4: 208-214.
2. Lardo A C, McVeigh E R, Jumrussirikul P, Berger R D, Calkins H, Lima J, Halperin H R. Visualization and Temporal/Spatial Characterization of Cardiac Radiofrequency Ablation Lesions Using Magnetic Resonance Imaging. Circulation 2000; 102; 698-705.
3. Dickfeld T, Kato R, Zviman M, Lai S, Meininger G, M D, Lardo A C, Roguin A, Blumke D, Berger R, Calkins H, Halperin H. Characterization of Radiofrequency Ablation Lesions With Gadolinium-Enhanced Cardiovascular Magnetic Resonance Imaging. J Am Coll Cardiol 2006; 47: 370-378.
4. Badger T J, Oakes R S, Daccarett M, Burgon N S, Akoum N, Fish E N, Blauer J J E, Rao S N, Adjei-Poku Y, Kholmovski E G, Vijayakumar S, Di Bella E V R, MacLeod R S, Marrouche N F. Temporal left atrial lesion formation after ablation of atrial fibrillation. Heart Rhythm 2009; 6: 161-168.
5. Taclas J E, Nezafat R, Wylie J V, Josephson M E, Hsing J, Manning W J, Peters D C. Relationship between intended sites of RF ablation and post-procedural scar in AF patients, using late gadolinium enhancement cardiovascular magnetic resonance. Heart Rhythm 2010; 7: 489-496.
6. Knowles B R, Caulfield D, Cooklin M, Rinaldi C A, Gill J, Bostock J, Razavi R, Schaeffter T, Rhode K S. 3-D Visualization of Acute RF Ablation Lesions Using MRI for the Simultaneous Determination of the Patterns of Necrosis and Edema. IEEE Trans. Biomed. Eng. 2010; 57(6): 1467-1475.
7. Shmatukha A, Qi X, Ghate S, Pop M, Barry J, Oduneye S, Stainsby J, Wright G, Crystal E. High-resolution MRI of RF lesion temporal evolution. In Proceedings of the 8$^{th}$ Interventional MRI Symposium, Leipzig, Germany, 24-25 Sep. 2010. p. 237-239.
8. Kim S H, Jung S E, Kim H L, Hahn S T, Park G S, Park W C. The potential role of dynamic MRI in assessing the effectiveness of high-intensity focused ultrasound ablation of breast cancer. Int. J. Hyperthermia, September 2010; 26(6): 594-603.
9. Breen M S, Lazebnik R S, Fitzmaurice M, Nour S G, Lewin J S, Wilson D L. Radiofrequency Thermal Ablation: Correlation of Hyperacute MR Lesion Images with Tissue Response. J Magn Reson Imaging 2004; 20: 475-486.
10. Kangasniemi M, Diederich C J, Price R E, Stafford R J, Schomer D F, Olsson L E, Tyreus P D, Nau W H, Hazle J D. Multiplanar MR Temperature-Sensitive Imaging of Cerebral Thermal Treatment Using Interstitial Ultrasound Applicators in a Canine Model. J Magn Reson Imaging 2002; 16: 522-531.
11. Yung J P, Shetty A, Elliott A, Weinberg J S, McNichols R J, Gowda A, Hazle J D, Stafford R J. Quantitative comparison of thermal dose models in normal canine brain. Med. Phys. 2010; 37(10): 5313-5321.
12. Cheng H-L, Purcell C M, Bilbao J M, Plewes D B. Prediction of Subtle Thermal Histopathological Change Using a Novel Analysis of Gd-DTPA Kinetics. J Magn Reson Imaging 2003; 18: 585-598.
13. Cheng H-L, Purcell C M, Bilbao J M, Plewes D B. Usefulness of Contrast Kinetics for Predicting and Monitoring Tissue Changes in Muscle Following Thermal Therapy in Long Survival Studies. J Magn Reson Imaging 2004; 19: 329-341.
14. Balvay D, Frouin F, Calmon G, Bessoud B, Kahn E, Siauve N, Clement O, Cuenod C-A. New Criteria for Assessing Fit Quality in Dynamic Contrast-Enhanced T1-Weighted MRI for Perfusion and Permeability Imaging. Magn Reson Med 2005; 54: 868-877.
15. Balvay D, Kachenoura N, Espinoza S, Thomassin-Naggara I, Fournier L S, Clement O, Cuenod C-A. Signal-to-Noise Ratio Improvement in Dynamic Contrast-enhanced CT and MR Imaging with Automated Principal Component Analysis Filtering. Radiology 2011; 258(2): 435-445.
16. Gianfelice D, Khiat A, Amara M, Belblidia A, Boulanger Y. MR imaging-guided focused ultrasound surgery of breast cancer: correlation of dynamic contrast-enhanced MRI with histopathologic findings. Breast Cancer Research and Treatment 2003; 82: 93-101.
17. Khiat A, Gianfelice D, Amara M, Boulanger Y. Influence of post-treatment delay on the evaluation of the response to focused ultrasound surgery of breast cancer by dynamic contrast enhanced MRI. The British Journal of Radiology 2006; 79: 308-314.
18. Shmatukha A, Sundaram B, Qi X, Oduneye S, Stainsby J, Wright G, Crystal E. Visualization of ablation lesions by dynamic contrast-enhanced (dynamic contrast enhancement) MRI. In Proceedings of the 13$^{th}$ Annual SCMR Scientific Sessions; Phoenix, Ariz., USA; 21-24 Jan. 2010. Journal of Cardiovascular Magnetic Resonance 2010; 12 (Suppl. 1): 025.
19. Shmatukha A, Crystal E. Automatic segmentation of ablation lesions and termination of the image acquisition/analysis process. In Abstracts of the 2011 SCMR/Euro CMR Joint Scientific Sessions; Nice, France, 3-6 Feb. 2011. Journal of Cardiovascular Magnetic Resonance 2011; 13 (Suppl. 1): P245.
20. Lazebnik R S, Weinberg B D, Breen M S, Lewin J S, Wilson D L. Semiautomatic Parametric Model-Based 3D Lesion Segmentation for Evaluation of MR-Guided Radiofrequency Ablation Therapy. Acad Radiol 2005; 12: 1491-1501.
21. Haacke M E, Brown R W, Thompson M R, Venkatesan R. Magnetic Resonance Imaging. Physical Principles and Sequence Design. New York: Wiley-Liss; 1999. pp. 374 (Eqs. 15.74 and 15.75) and 876 (Eq. B.20).
22. Bernstein M A, Thomasson D M, Perman W H. Improved detectability in low signal-to-noise ratio magnetic resonance images by means of a phase-corrected real reconstruction. Med. Phys. September/October 1989; 16(5): 813-817.
23. Gudbjartsson H, Patz S. The Rician Distribution of Noisy MRI Data. Magn Reson Med 1995; 34: 910-914.

24. Haacke M E, Brown R W, Thompson M R, Venkatesan R. Magnetic Resonance Imaging. Physical Principles and Sequence Design. New York: Wiley-Liss; 1999. p. 455 (Eq. 18.14) and p. 367 (Eqs. 15.62 and 15.63).
25. Otsu N. A Threshold Selection Method from Gray-Level Histograms. IEEE Transactions on System, Man, and Cybernetics January 1979; SMC-9(1): 62-66.
26. Dougherty G. Digital Image Processing for Medical Applications. New York: Cambridge University Press; 2009. p. 275-283.
27. R L Ehman, J P Felmlee, Adaptive technique for high definition MR imaging of moving structures, Radiology, 173, 255, (1989)

Therefore what is claimed is:

1. A method of performing contrast-enhanced medical imaging, the method including the steps of:
    a) prior to injection of a contrast agent to a subject, acquiring one or more baseline images of the subject with an imaging device;
    b) processing the baseline image data to determine an average baseline image from the one or more baseline images; and
    during or after injection of the contrast agent to the subject;
    c) acquiring a post-injection image with the imaging device;
    d) processing image data from previously acquired post-injection images to generate at least one cumulative map, wherein a baseline contribution is removed based on the average baseline image;
    e) determining a frequency of occurrence of cumulative map values of pixels within binned intervals in a form suitable for generating a histogram;
    f) determining a quantity associated with a double-peak shape of the histogram and comparing the quantity to a pre-determined threshold, wherein each peak of the double-peak shape is associated with tissue having a different perfusion rate;
    g) repeating steps c) to f) until the quantity exceeds the pre-determined threshold; and
    h) segmenting the most recently generated cumulative map to generate a segmented image for visualizing a border between tissue regions having different perfusion characteristics;
    wherein steps b), d), e), f) and h) are performed using one or more processors.

2. The method according to claim 1 further comprising the step of interrupting image acquisition after the quantity exceeds the pre-determined threshold.

3. The method according to claim 1 wherein the step of segmenting the cumulative map is performed by separating pixels in the histogram by selecting pixels according to a pre-defined criterion.

4. The method according to claim 3 wherein the pre-defined criterion includes the pre-determined threshold.

5. The method according to claim 1 wherein the pre-determined threshold is associated with a contrast-to-noise ratio that is suitable for subsequent image analysis.

6. The method according to claim 1 wherein image data is obtained for a plurality of slices, and wherein the step of generating a cumulative map includes generating a per-slice cumulative map for each slice.

7. The method according to claim 6 wherein the step of generating a histogram associated with the cumulative map includes generating a per-slice histogram for two or more of the slices, and wherein the step of determining a quantity associated with the double-peak shape of the histogram includes determining a per-slice quantity for each of the two or more slices, and wherein the step of comparing the quantity to a pre-determined threshold includes the step of comparing the per-slice quantities to the pre-determined threshold.

8. The method according to claim 7 wherein the step of comparing the per-slice quantities to the pre-determined threshold includes calculating an average value of the per-slice quantities and comparing the average value of the per-slice quantities to the pre-determined threshold.

9. The method according to claim 8 wherein the average value is calculated as a weighted average using pre-defined weights.

10. The method according to claim 7 wherein the two or more slices are selected to be slices of physiological or anatomical importance.

11. The method according to claim 6 wherein the step of generating a histogram associated with the cumulative map includes generating a per-slice histogram for two or more of the slices, and wherein the step of determining a quantity associated with the double-peak shape of the histogram includes determining a per-slice quantity for each of the two or more slices, and wherein the step of comparing the quantity to a pre-determined threshold includes the step of comparing the per-slice quantities to corresponding per-slice thresholds.

12. The method according to claim 1 wherein step d) further includes correcting for a bias in the cumulative map.

13. The method according to claim 12 wherein the bias correction is based on the average baseline image and iteratively accumulated terms.

14. The method according to claim 12 wherein the step of correcting for the bias includes adding, to the cumulative map, a term proportional to the number of post-injection images.

15. The method according to claim 14 wherein the term is also proportional to a summation of the differences between the measured intensity and the average baseline image intensity for the baseline images obtained prior to injection of the contrast agent.

16. The method according to claim 1 wherein the step of generating the cumulative map includes performing a calculation based on a previously generated cumulative map and a newly acquired post-injection image.

17. The method according to claim 1 wherein the cumulative map is a cumulative intensity difference map.

18. The method according to claim 17 wherein step of generating the cumulative intensity difference map includes calculating differences between each post-injection image and the average baseline image, and summing the differences.

19. The method according to claim 1 wherein the cumulative map is a cumulative intensity ratio map.

20. The method according to claim 19 wherein step of generating the cumulative intensity ratio map includes calculating ratios of intensities between each post-injection image and the average baseline image and summing the ratios.

21. The method according to claim 1 wherein the cumulative map is a cumulative enhancement sum based on a cumulative intensity difference map and a cumulative intensity ratio map.

22. The method according to claim 21 wherein the cumulative intensity difference map and the cumulative intensity ratio map are normalized to a common dynamic range.

23. The method according to claim 1 wherein the at least one cumulative map is two or more cumulative maps.

24. The method according to claim 1 wherein the cumulative map includes image data from all previously acquired post-injection images.

25. The method according to claim 1 wherein when performing step d) for the first time, the previously acquired post-injection images is the first post-injection image.

26. The method according to claim 1 wherein the images are obtained according to an imaging modality selected from the group consisting of magnetic resonance imaging, ultrasound imaging, computed tomography, SPECT, PET, x-ray, nuclear perfusion modalities, and optical imaging modalities.

27. The method according to claim 1 wherein the quantity associated with the double-peak shape of the histogram is selected from the group consisting of a ratio between the peak-valley offset and the average peak height, the horizontal separation of the peaks, the peak values, the peak positions, the width of the peaks, and one or more fitting parameters obtained from fitting the double-peak structure to a mathematical function.

28. A computer implemented method of automating acquisition of dynamic contrast-enhanced medical images, the method including the steps of:
 a) acquiring, with an imaging device, baseline image data including one or more baseline images of the subject prior to injection of contrast agent;
 b) processing the baseline image data to determine an average baseline image;
 c) acquiring a post-injection image with the imaging device;
 d) processing image data from previously acquired post-injection images to generate at least one cumulative map and removing a baseline contribution based on the average baseline image;
 e) determining a frequency of occurrence of cumulative map values of pixels within binned intervals in a form suitable for generating a histogram;
 f) determining a quantity associated with a double-peak shape of the histogram and comparing the quantity to a pre-determined threshold, wherein each peak of the double-peak shape is associated with tissue having a different perfusion rate;
 g) repeating steps c) to f) until the quantity exceeds the pre-determined threshold; and
 h) segmenting the most recently generated cumulative map to generate a segmented image for visualizing a border between tissue regions having different perfusion characteristics;
 wherein steps b), d), e), f) and h) are performed using one or more processors.

29. A non-transitory computer-readable storage medium comprising instructions for automating acquisition of dynamic contrast-enhanced medical images, wherein execution of the instructions by one or more processors causes the one or more processors to carry out the steps of:
 a) acquiring, with an imaging device, baseline image data including one or more baseline images of the subject prior to injection of contrast agent;
 b) processing the baseline image data to determine an average baseline image;
 c) acquiring a post-injection image with the imaging device;
 d) processing image data from previously acquired post-injection images to generate at least one cumulative map wherein a baseline contribution is removed based on the average baseline image;
 e) determining a frequency of occurrence of cumulative map values of pixels within binned intervals in a form suitable for generating a histogram;
 f) determining a quantity associated with a double-peak shape of the histogram and comparing the quantity to a pre-determined threshold, wherein each peak of the double-peak shape is associated with tissue having a different perfusion rate;
 g) repeating steps c) to f) until the quantity exceeds the pre-determined threshold; and
 h) segmenting the most recently generated cumulative map to generate a segmented image for visualizing a border between tissue regions having different perfusion characteristics;
 wherein steps b), d), e), f) and h) are performed using one or more processors.

30. A method of performing dynamic contrast-enhanced medical imaging, the method including the steps of:
 a) acquiring, with an imaging device, one or more baseline images of a subject prior to injection of contrast agent, and determining an average baseline image;
 during or after injection of the contrast agent to the subject:
 b) acquiring a post-injection image with the imaging device;
 c) processing image data from previously acquired post-injection images to generate at least one cumulative map including image data from previously acquired post-injection images, wherein a baseline contribution is removed based on the average baseline image;
 d) determining a frequency of occurrence of cumulative map values of pixels within binned intervals in a form suitable for generating a histogram;
 e) determining a quantity associated with a double-peak shape of the histogram and comparing the quantity to a pre-determined threshold, wherein each peak of the double-peak shape is associated with tissue having a different perfusion rate; and
 f) repeating steps b) to e) until the quantity exceeds the pre-determined threshold; and
 g) segmenting the most recently generated cumulative map to generate a segmented image for visualizing a border between tissue regions having different perfusion characteristics;
 wherein steps c), d), e) and g) are performed using one or more processors.

31. A method of performing contrast-enhanced medical imaging, the method including the steps of:
 a) prior to injection of a contrast agent to a subject, acquiring one or more baseline images of the subject with an imaging device;
 b) processing the baseline image data to determine an average baseline image from the one or more baseline images; and
 during or after injection of the contrast agent to the subject;
 c) acquiring, with the imaging device, a plurality of post-injection images;
 d) processing image data from the post-injection images to generate at least one cumulative map, wherein a baseline contribution is removed based on the average baseline image;
 e) correcting for a bias in the cumulative map; and
 f) segmenting the cumulative map generate a segmented image for visualizing a border between tissue regions having different perfusion characteristics;
 wherein the cumulative map is a cumulative enhancement sum based on a cumulative intensity difference map and a cumulative intensity ratio map; and
 wherein steps b), d), e) and f) are performed using one or more processors.

32. The method according to claim 31 wherein the bias correction is based on the average baseline image and iteratively accumulated terms.

33. The method according to claim 31 wherein the step of correcting for the bias includes adding, to the cumulative map, a term proportional to the number of post-injection images.

34. The method according to claim 33 wherein the term is also proportional to a summation of the differences between the measured intensity and the average baseline image intensity for the baseline images obtained prior to injection of the contrast agent.

35. The method according to claim 31 further comprising repeating steps c) through d) one or more times.

36. A computer implemented method of processing dynamic contrast-enhanced medical images, the method including the steps of:
   a) acquiring, with an imaging device, baseline image data including one or more baseline images of a subject;
   b) processing the baseline image data to determine an average baseline image;
   c) acquiring, with the imaging device, a plurality of post-injection images;
   d) processing image data from the post-injection images to generate at least one cumulative map, and removing a baseline contribution based on the average baseline image;
   e) processing the cumulative map data and the baseline image data to correct for a bias in the cumulative map; and
   f) segmenting the cumulative map to obtain generate a segmented image for visualizing a border between tissue regions having different perfusion characteristics;
   wherein the cumulative map is a cumulative enhancement sum based on a cumulative intensity difference map and a cumulative intensity ratio map; and
   wherein steps b), d), e) and f) are performed using one or more processors.

37. A method of performing contrast-enhanced medical imaging, the method including the steps of:
   a) prior to injection of a contrast agent to a subject, acquiring one or more baseline images of the subject with an imaging device;
   b) processing the baseline image data to determine an average baseline image from the one or more baseline images; and
   during or after injection of the contrast agent to the subject;
   c) acquiring a post-injection image with the imaging device;
   d) processing image data from previously acquired post-injection images to generate at least one cumulative map, wherein a baseline contribution is removed based on the average baseline image;
   e) determining a frequency of occurrence of cumulative map values of pixels within binned intervals in a form suitable for generating a histogram;
   f) determining a quantity associated with a shape of the histogram and comparing the quantity to a pre-determined threshold;
   g) repeating steps c) to f) until the quantity exceeds the pre-determined threshold; and
   h) segmenting the most recently generated cumulative map to generate a segmented image for visualizing a border between tissue regions having different perfusion characteristics;
   wherein the cumulative map is a cumulative enhancement sum based on a cumulative intensity difference map and a cumulative intensity ratio map; and
   wherein steps b), d), e), f) and h) are performed using one or more processors.

* * * * *

UNITED STATES PATENT AND TRADEMARK OFFICE
CERTIFICATE OF CORRECTION

PATENT NO. : 9,095,273 B2  
APPLICATION NO. : 13/245591  
DATED : August 4, 2015  
INVENTOR(S) : Andriy Shmatukha and Eugene Crystal It is certified that error appears in the above-identified patent and that said Letters Patent is hereby corrected as shown below:

Claims

Column 28, Line 10

In claim 9 of the Letter Patent, line 2, "as a weighted average" should be deleted as shown below:

9. The method according to claim 8 wherein the average value is calculated using pre-defined weights.

Signed and Sealed this  
Fifth Day of April, 2016

Michelle K. Lee  
*Director of the United States Patent and Trademark Office*